(12) United States Patent
Sowb

(10) Patent No.: US 10,136,813 B2
(45) Date of Patent: Nov. 27, 2018

(54) SYSTEMS AND METHODS FOR PATIENT CARDIOVASCULAR AND RESPIRATORY MANAGEMENT

(76) Inventor: Yasser A. Sowb, West Sacramento, CA (US)

( * ) Notice: Subject to any disclaimer, the term of this patent is extended or adjusted under 35 U.S.C. 154(b) by 505 days.

(21) Appl. No.: 12/764,031

(22) Filed: Apr. 20, 2010

(65) Prior Publication Data

US 2010/0262116 A1 Oct. 14, 2010

Related U.S. Application Data

(63) Continuation-in-part of application No. PCT/US2008/080564, filed on Oct. 20, 2008.
(Continued)

(51) Int. Cl.
*A61B 5/00* (2006.01)
*A61B 5/0205* (2006.01)
(Continued)

(52) U.S. Cl.
CPC .............. *A61B 5/00* (2013.01); *A61B 5/0205* (2013.01); *A61B 5/4839* (2013.01);
(Continued)

(58) Field of Classification Search
CPC . A61B 5/0205; A61B 5/0022; A61B 5/02055; A61B 5/021; A61B 5/7264; A61B 5/742; A61B 5/1128; A61B 5/743; A61B 5/0002; A61B 5/0006; A61B 5/024; A61B 5/1118; A61B 5/7275; A61B 2560/0242; A61B 5/02; A61B 5/00; A61B 5/4839; A61B 5/7445; A61M 1/3639; A61M 2205/502; A61M 2039/242; A61M 39/22;
(Continued)

(56) References Cited

U.S. PATENT DOCUMENTS 5,370,122 A * 12/1994 Kunig ................. A61B 5/0205
600/481
5,447,161 A 9/1995 Blazek et al.
(Continued)

FOREIGN PATENT DOCUMENTS

| JP | 11-232359 A | 8/1999 |
|----|---|---|
| WO | WO 2009/052530 | 4/2009 |
| WO | WO 2009/052532 | 4/2009 |

OTHER PUBLICATIONS

PCT Patent Application No. PCT/US2008/080564 filed Oct. 20, 2008 in the name of Sowb, International Search Report and Written Opinion dated Dec. 19, 2008.
(Continued)

*Primary Examiner* — Brandy S Lee
(74) *Attorney, Agent, or Firm* — Levine Bagade Han LLP

(57) ABSTRACT

An information display and control system that enables a fast and easy understanding and management of the status of the patient's cardiovascular and ventilation systems is disclosed. The system can control administration and management of a patient's medication and fluids. The display is organized by goals related to management of patient's cardiovascular system, ventilation system, and medications and fluids administration and management. Such goals include hemodynamics, oxygenation, $CO_2$ removal, medication status, and fluids status.

20 Claims, 15 Drawing Sheets

Related U.S. Application Data

(60) Provisional application No. 61/000,150, filed on Oct. 20, 2007.

(51) Int. Cl.
| | | |
|---|---|---|
| *A61M 5/142* | (2006.01) | |
| *A61M 5/172* | (2006.01) | |
| *G16H 40/63* | (2018.01) | |
| *G06F 19/00* | (2018.01) | |

(52) U.S. Cl.
CPC ........... *A61B 5/7445* (2013.01); *A61M 5/142* (2013.01); *A61M 5/1723* (2013.01); *G06F 19/00* (2013.01); *G16H 40/63* (2018.01); *A61M 2005/14208* (2013.01)

(58) Field of Classification Search
CPC .............. A61M 5/007; A61M 5/14212; A61M 5/1452; A61M 5/16827; A61M 5/172; A61M 2005/14208; A61M 5/142; A61M 5/1723; G16H 40/63; G06F 19/00
USPC .......................... 604/500; 345/440; 382/131
See application file for complete search history.

(56) References Cited

U.S. PATENT DOCUMENTS

| | | | |
|---|---|---|---|
| 5,859,885 A | 1/1999 | Rusnica et al. | |
| 5,921,920 A | 7/1999 | Marshall et al. | |
| 6,234,963 B1 | 5/2001 | Blike et al. | |
| 6,409,675 B1 * | 6/2002 | Turcott | 600/508 |
| 6,743,172 B1 | 6/2004 | Blike | |
| 6,860,266 B2 | 3/2005 | Blike | |
| 6,985,771 B2 | 1/2006 | Fischell et al. | |
| 7,413,546 B2 | 8/2008 | Agutter et al. | |
| 2002/0123671 A1 | 9/2002 | Haaland | |
| 2003/0036744 A1 | 2/2003 | Struys et al. | |
| 2003/0055344 A1 | 3/2003 | Eigler et al. | |
| 2003/0055356 A1 | 3/2003 | Nonaka | |
| 2003/0114786 A1 | 6/2003 | Hiller et al. | |
| 2003/0156143 A1 * | 8/2003 | Westenskow et al. | 345/848 |
| 2004/0220637 A1 | 11/2004 | Zdeblick et al. | |
| 2005/0010117 A1 | 1/2005 | Agutter et al. | |
| 2005/0139213 A1 | 6/2005 | Blike | |
| 2005/0187461 A1 * | 8/2005 | Murphy et al. | 600/416 |
| 2005/0277912 A1 | 12/2005 | John | |
| 2006/0064026 A1 * | 3/2006 | Hirsh | 600/508 |
| 2006/0111749 A1 | 5/2006 | Westenskow et al. | |
| 2006/0161071 A1 * | 7/2006 | Lynn et al. | 600/538 |
| 2006/0241977 A1 * | 10/2006 | Fitzgerald et al. | 705/3 |
| 2007/0027368 A1 | 2/2007 | Collins et al. | |
| 2007/0178167 A1 | 2/2007 | Andrijauskas | |
| 2007/0050715 A1 * | 3/2007 | Behar | A61B 5/0002 715/706 |
| 2007/0188494 A1 | 8/2007 | Agutter et al. | |
| 2007/0191724 A1 | 8/2007 | Hirsh | |
| 2007/0197978 A1 | 8/2007 | Wortham | |
| 2008/0033661 A1 * | 2/2008 | Syroid | A61B 5/00 702/22 |
| 2008/0234322 A1 | 9/2008 | Syroid et al. | |

OTHER PUBLICATIONS

PCT Patent Application No. PCT/US2008/080562 filed Oct. 20, 2008 in the name of Sowb, International Search Report and Written Opinion dated Jan. 2, 2009.

* cited by examiner

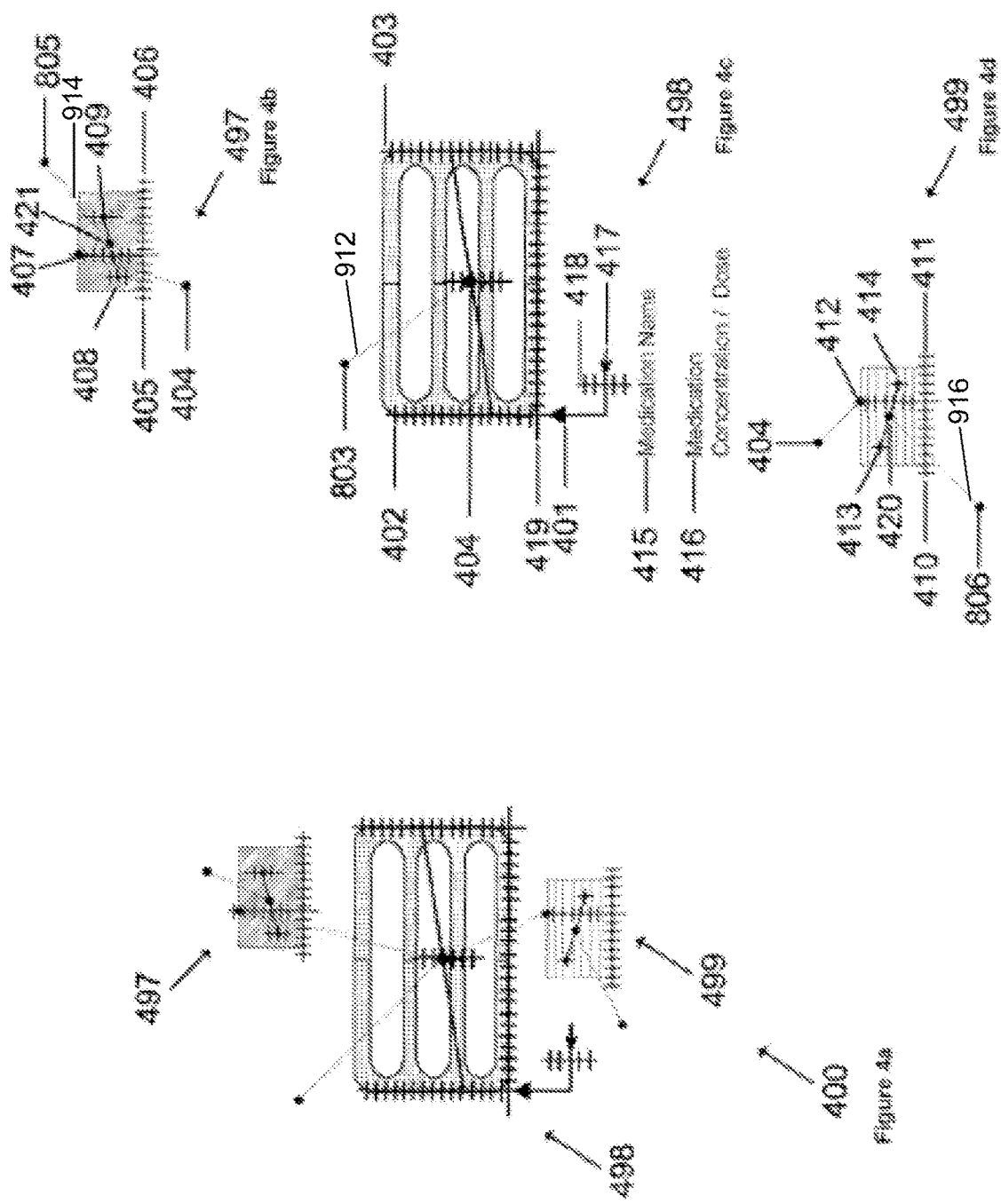

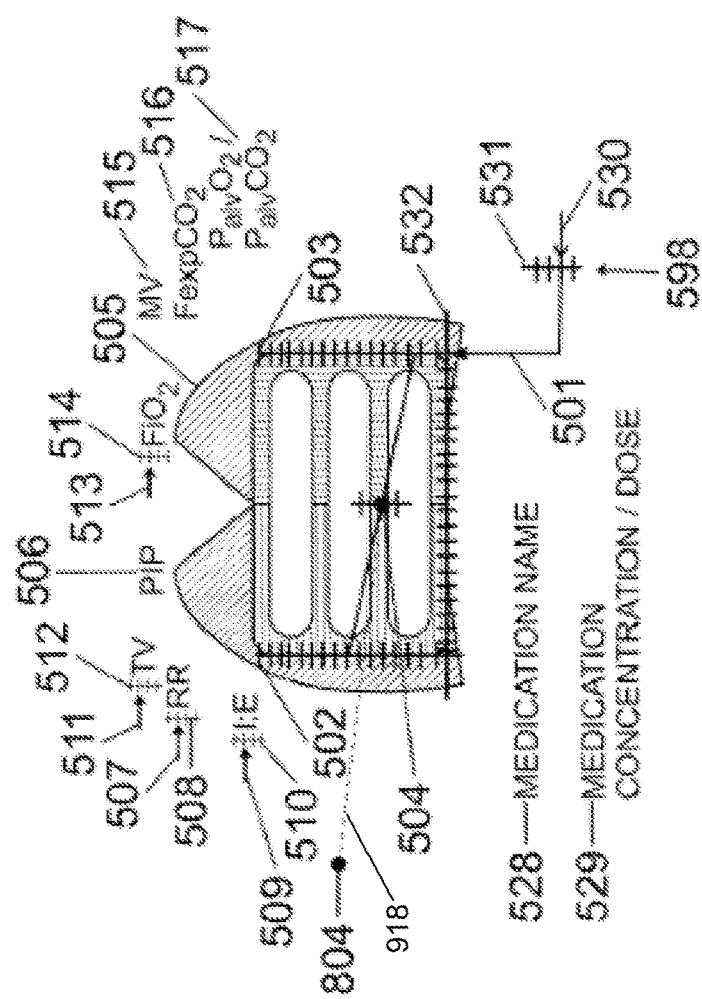
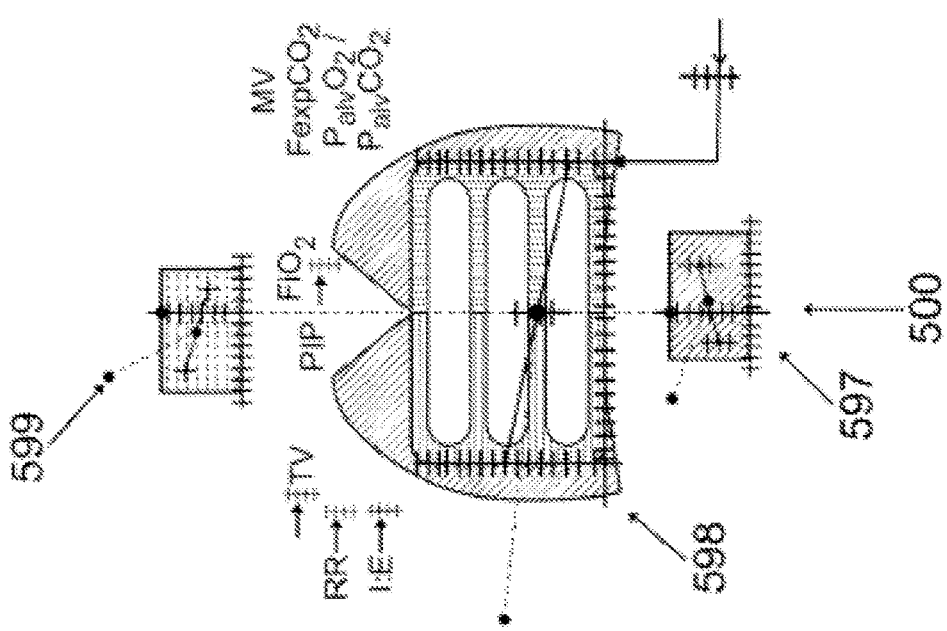
Figure 5c
Figure 5a

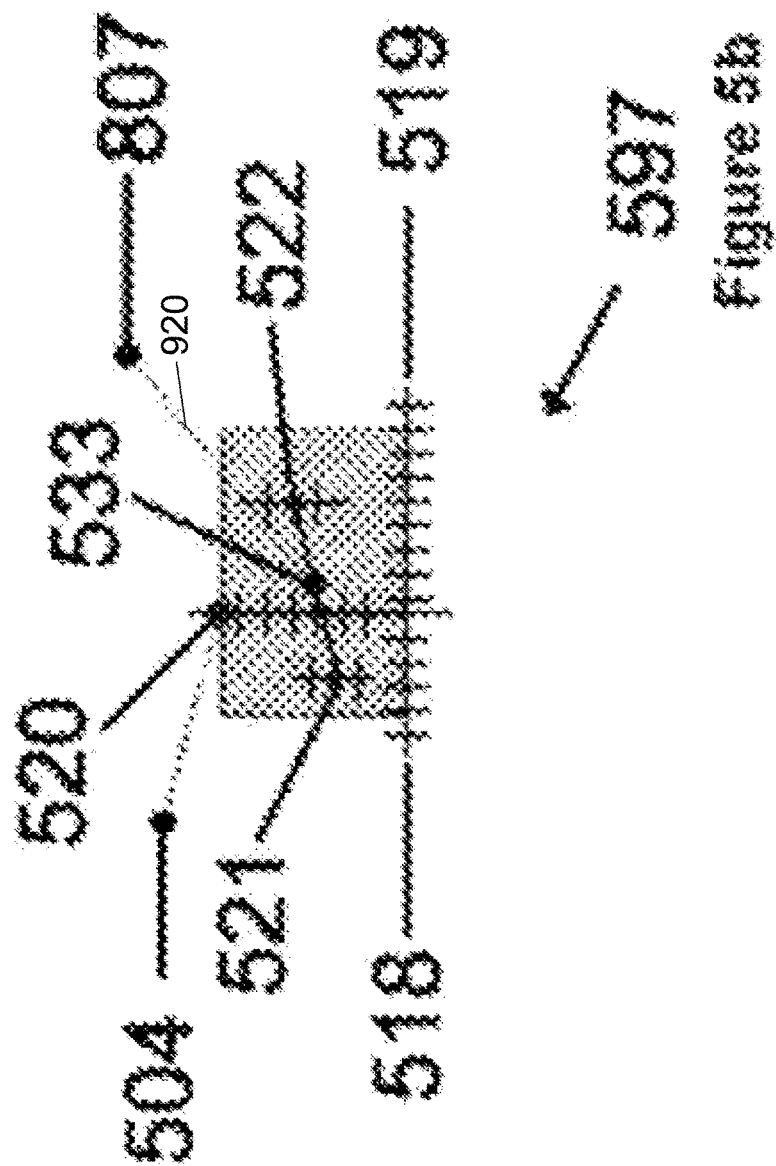

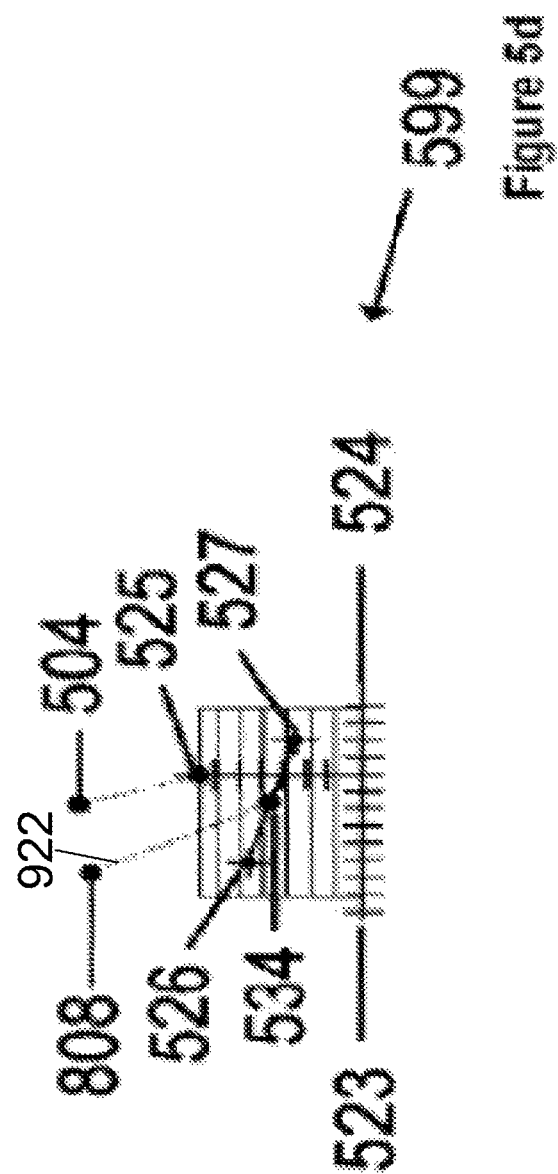

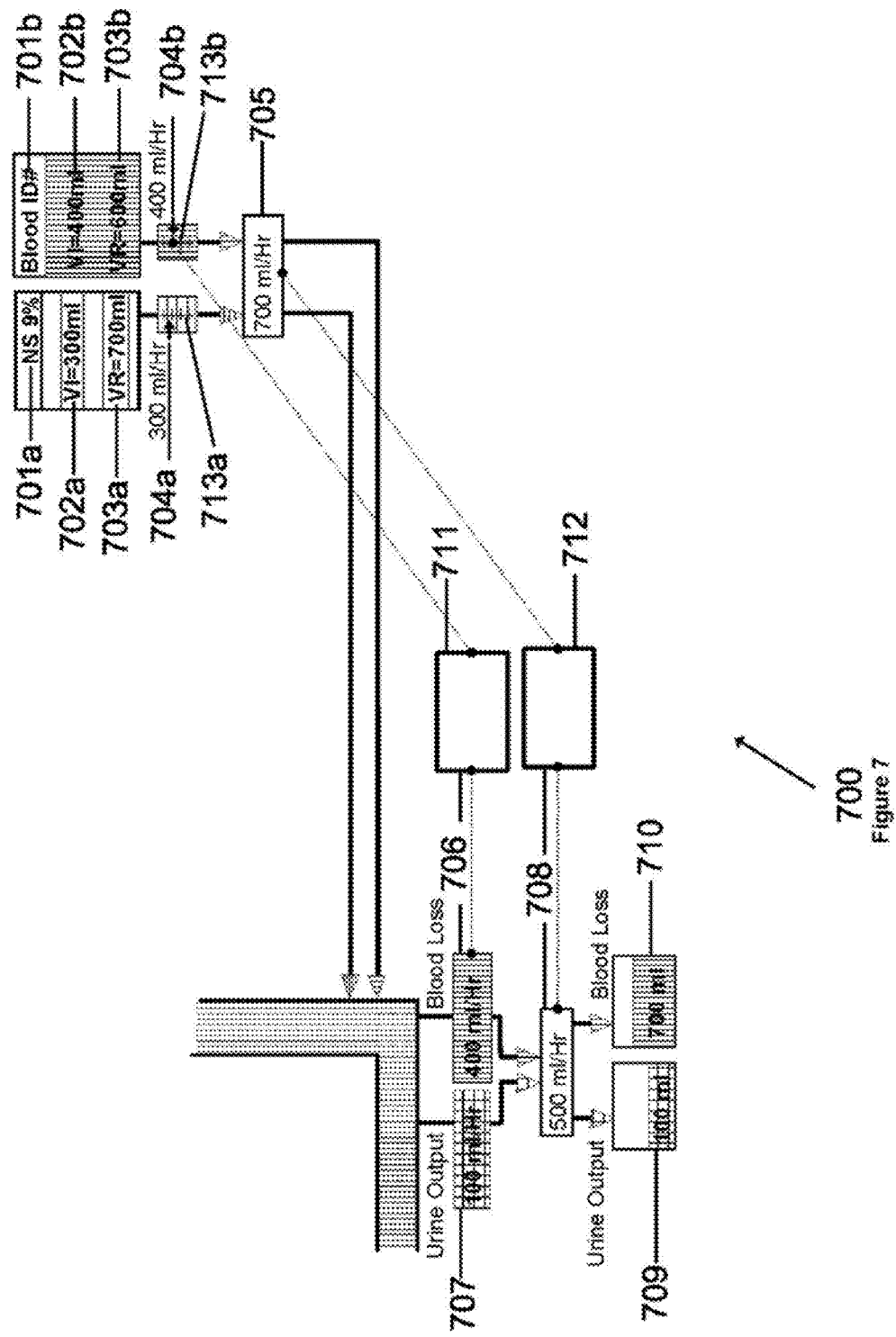

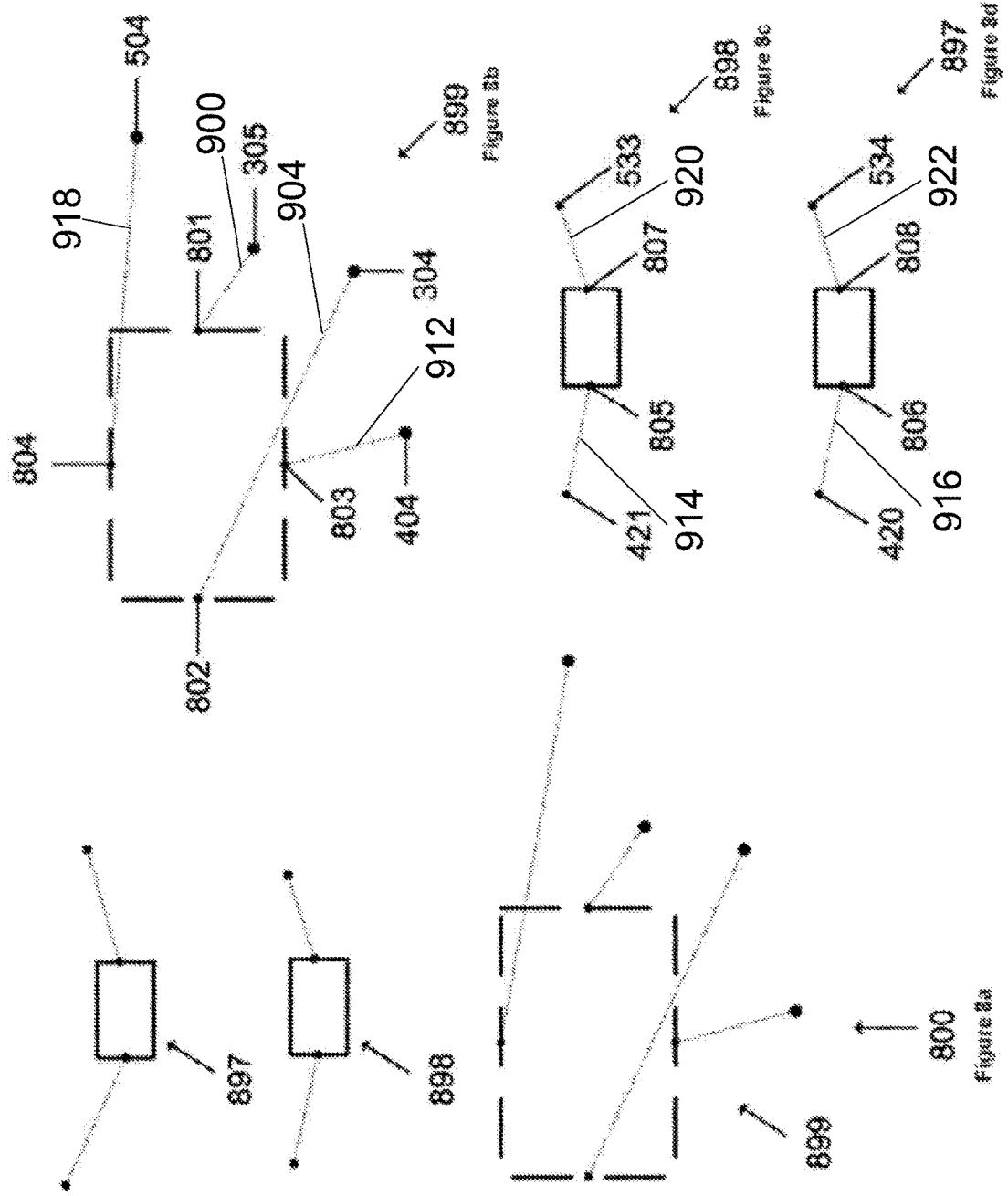

SYSTEMS AND METHODS FOR PATIENT CARDIOVASCULAR AND RESPIRATORY MANAGEMENT

CROSS REFERENCE TO RELATED APPLICATION

This application is a continuation-in-part of International Application No. PCT/US2008/080564 filed Oct. 20, 2008 which claims benefit of priority to U.S. Provisional Application No. 61/000,150, filed Oct. 20, 2007, both of which are incorporated herein by reference in their entireties.

BACKGROUND OF THE INVENTION

1. Field of the Invention

The present invention relates to management, display and information presentation and decision-support systems used to improve attention allocation, situation awareness, problem solving and decision making during management of patient's cardiovascular and ventilation systems and during administration and management of patient's medications and fluids.

2. Description of the Prior Art

Human error results when available resources of the clinician, such as knowledge, skills, and strategies, are inadequate for the demands of the situation. In medicine, monitoring equipment and their displays extend the physician's resources but at the expense of additional cognitive demands. Clinicians' abilities to meet the demands of critical decision making during management of patient's cardiovascular system and during administration and management of patient's medication and fluids depend not only on their internal resources, but also on the displays through which they perceive the situation. Although some patient and equipment indicators are observed and measured directly by the clinician, increasing, the data used to diagnose and correct critical situations are measured and displayed by medical equipment.

Most medical informational displays are traditional, in that they are based on the one-sensor/one-indicator technology. Research in other domains has shown that such display design is not compatible with the capabilities of the human perceptual system, and may hinder data transmission from the machine to the human. Traditional numeric and meter displays do not take advantage of people's inherent ability to understand patterns and shapes. During routine and problem-solving situations, the human must scan many displays to collect relevant data. Traditionally, data is displayed in a single format, even though the relevance of the data changes with the goals of the situation. Traditional displays have high attention demands since insignificant information may be prominent while important data are pushed into the background. Since traditional displays do not directly display the high-order state of the system, the clinician problem-solver must deduce system state by processing raw data, in the form of machine-sensed variables, directly-sensed indicators, and situational cues. Furthermore, the functional relationships among the various elemental display elements are not represented and calculations are sometimes required to derive such high-order state properties. Traditional displays require considerable effort and knowledge which may exceed the human's capabilities or the time available for effective action.

In other complex domains, new management and display systems, called ecological interface systems, have been developed to reduce human error and support the clinician's attentional and problem solving and decision-making demands. Ecological Interface Design (EID) has been proposed as a method for creating human-machine equipment that make work processes more visible and aid the human during complex management and problem-solving situations. In ecological interface systems, elements are organized to show inter-relationships among system variables. The interface is organized in two dimensions: abstraction hierarchy and system decomposition. In the abstraction hierarchy, the highest level contains operator goals, middle levels represent system functions, and the lowest level specifies the system's controls and physical form. In system decomposition, the highest level represents the whole system, middle levels describe subsystems, and the lowest level deals with components. Thus, the system contains controls and representations of everything the operator needs to consider in performing his or her work, from abstract goals to physical actions, whether dealing with the entire system or considering specific components.

Ecological interface systems present the operator with a complete set of the goals to be achieved in managing the system, the rules or the constraints that govern these goals, and the low-level variables or data that are processed by these rules. By making system processes visible, ecological interface systems support various tasks, such as process control, safety monitoring, and fault diagnosis. Safety monitoring is performed high in the abstraction dimension to detect violated goals. Fault diagnosis is accomplished by moving down the abstraction hierarchy, along the paths of violated goals, to detect the rules that have been broken. Further down the hierarchy are the controls or variables to be manipulated in order to correct the event. Ecological interface systems have been utilized in nuclear and petrochemical process applications, but have not been widely used and applied to medical systems. In this patent application, we apply the EID principles to design a system for management of patient's cardiovascular and ventilation system and for the administration and management of patient's medications and fluids.

SUMMARY OF THE INVENTION

A human-machine system for use for management of patient's cardiovascular and ventilation systems and the administration and management of patient's medications and fluids is disclosed having the capability of design and configuration of a display of the goals and objectives, processes and functions, and components and controls comprising management of patient's cardiovascular and ventilation systems and the administration and management of patient's medications and fluids. The system utilizes several levels of abstraction hierarchies to present to the user goals, middle- and lower-level functional parameters, and lower-level components and controls used in monitoring and controlling the cardiovascular and ventilation systems and in the administration and management of patient's medications and fluids. The system presents to the user:

1. The higher-level goals and objectives of managing the cardiovascular and ventilation systems and for the administration and management of patient's medications and fluids.
2. The middle- and lower-level functional parameters and variables used during monitoring and controlling the cardiovascular and ventilation systems and during the administration and management of patient's medications and fluids.

3. The lower-level components and controls used during monitoring and controlling the cardiovascular and ventilation systems and during the administration and management of patient's medications and fluids.
4. The inter-relationships between the goals and objectives, the functional parameters or variables, and the lower-level component and controls used for monitoring and controlling the cardiovascular and ventilation systems and for the administration and management of patient's medications and fluids.

The system maps such goals and objectives, functional parameters or variable, lower-level components and controls, and the inter-relationships between the goals, the functional parameters or variables, and the lower-level component and controls onto an anatomical graphical representation of the cardiovascular and ventilation systems. The anatomical graphical representation of the cardiovascular system shows the anatomy or layout of the cardiovascular system and its components including the heart, the systemic and pulmonary arterial and venous vascular systems, the blood, and the circulatory nature and appearance of the cardiovascular system. The anatomical graphical representation of the cardiovascular system also shows animation of the heart's contraction, and the blood flow with the cardiovascular system. The anatomical graphical representation of the ventilation system shows the lungs and animation of breathing or mechanical ventilation.

Furthermore, the system utilizes mass conservation principles to calculate and present to the user information pertaining to balance between the goals and objectives of managing the cardiovascular and ventilation systems within the different parts of the cardiovascular system. The system presents to the user information pertaining to the functional parameters or variable, and the interrelationships between them and the higher-level goals and lower-level controls of managing the cardiovascular and ventilation systems. The system utilizes mass conservation principles to calculate and present to the user information pertaining to balance between the goals and objectives of the administration and management of patient's medications and fluids. The system presents to the user information pertaining to the functional parameters or variable, and the interrelationships between them and the higher-level goals and lower-level controls of the administration and management of patient's medications and fluids. The system provides the user (clinicians, nurses, etc.) with real time data for process monitoring and control of patient's cardiovascular and ventilation systems to support management of patient's hemodynamics, ventilation, and the administration and management of medications and fluids. The system facilitates activities such as attention allocation, situation awareness, abstract reasoning, and hypothesis testing during management of the cardiovascular system and during the administration and management of patient's medications and fluids.

BRIEF DESCRIPTION OF THE DRAWINGS

FIG. 4a illustrates a variation of the systemic vascular displays and controls of the patient management system.

FIG. 4b illustrates a variation of the systemic vascular oxygenation display of the patient management system.

FIG. 4c illustrates a variation of the systemic vascular hemodynamics displays and controls of the patient management system.

FIG. 4d illustrates a variation of the systemic vascular carbon dioxide removal displays and controls of the patient management system.

FIG. 5a illustrates a variation of the pulmonary vascular displays and controls of the patient management system.

FIG. 5b illustrates a variation of the pulmonary vascular oxygenation displays and controls of the patient management system.

FIG. 5c illustrates a variation of the pulmonary vascular hemodynamics displays and controls of the patient management system.

FIG. 5d illustrates a variation of the pulmonary vascular carbon dioxide removal displays and controls of the patient management system.

FIG. 7 illustrates a variation of the fluids management display and controls of the patient management system.

FIG. 8a illustrates a variation of the hemodynamics, oxygen delivery-consumption, and carbon dioxide production-removal balance object displays of the patient management system.

FIG. 8b illustrates a variation of the hemodynamics balance object display of the patient management system.

FIG. 8c illustrates a variation of the oxygen delivery-consumption balance object display of the patient management system.

FIG. 8d illustrates a variation of the carbon dioxide production-removal balance object display of the patient management system.

DETAILED DESCRIPTION

A patient management system 150 is described. The patient management system 150 can monitor, control and communicate (e.g., visually display or audibly sound) patient physiological diagnosis, status and treatment. The system can have a human-machine interface for process monitoring and control of patient's cardiovascular and ventilation systems, and for the administration and management of patient's medications and fluids capable of the creation of displays and controls, wherein such displays are collections of one or more displays that may be graphs showing mathematical relationships or graphical in nature, and wherein such controls are collections of one or more controls that may be used to control patient's cardiovascular and ventilation systems, and for the administration and management of patient's medications and fluids using a touch screen, a mouse, keyboard, or any other human-machine interface control.

Figure 1A:
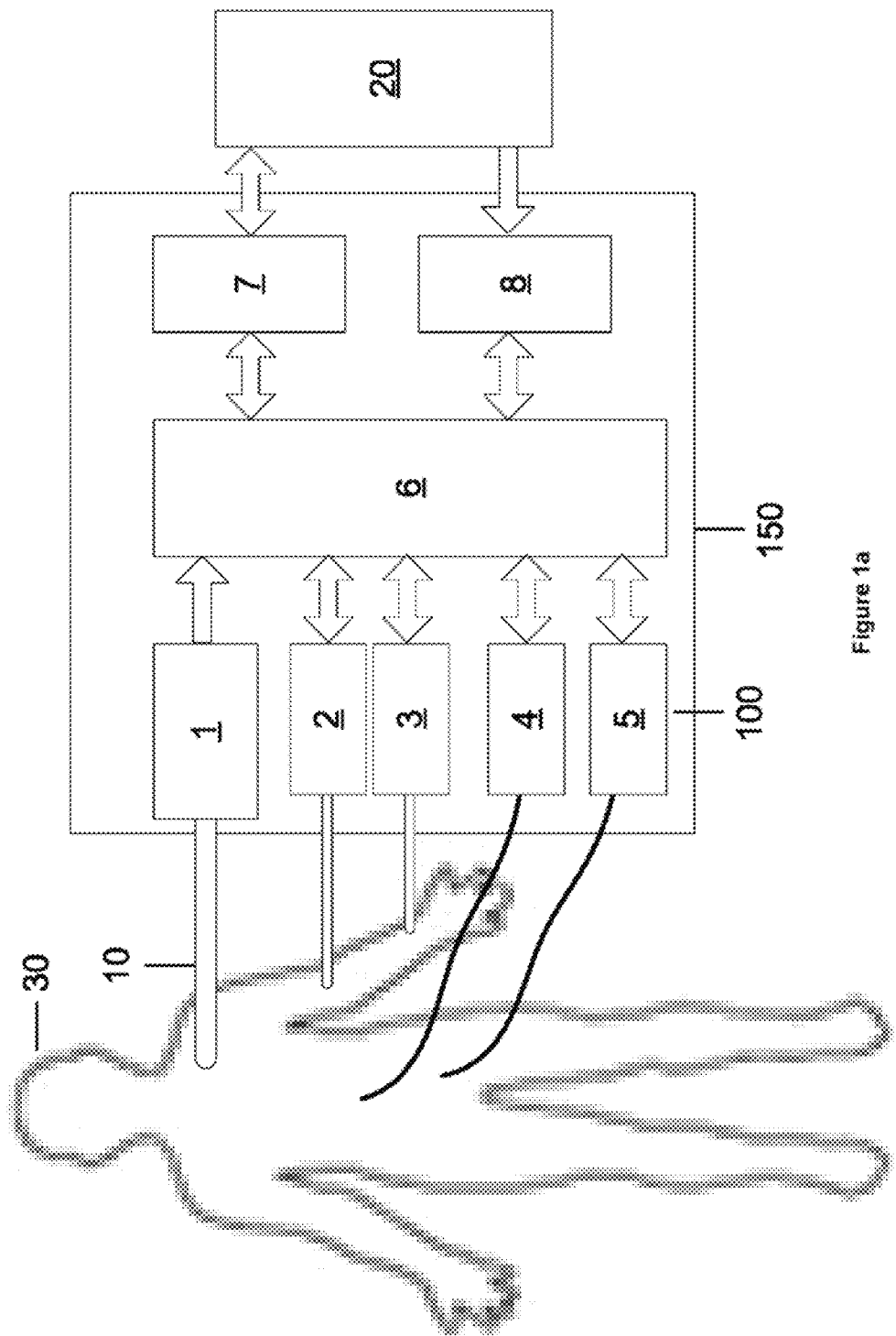
FIGS. 1a and 1b are schematic figures of variations of the patient management system.

System Components:

FIG. 1 illustrates that the management system 150 can have one or more direct subsystems 100, such as a monitoring system 1, a medication delivery system 2, an IV fluids delivery system 3, a bleeding system 4, a urine output system 5, or combinations thereof. The management system 150 can be for cardiovascular and respiratory management and administration and management of patient's medications and fluids. Any or all of the direct subsystems can be directly attached to the patient 30, for example by one or more probes 10. Any or all of the direct subsystems can be controlled by a micro-processor executing a management algorithm 6. The management algorithm 6 can display information through a one-way or two-way (e.g., touch screen) visual display monitor 7 and/or speakers (e.g., output speakers and/or one or more microphones). The management algorithm 6 can receive instructions from a control 8 which can be a separate input device (e.g., a keyboard, mouse or joystick), an integrated input device (e.g., the touch screen on the display monitor 7), or combinations thereof. The user 20 can provide instructions to the management algorithm 6 through the control 8, which can be part of the display 7.

The direct subsystems 100 can be physically integrated with the management algorithm 6, the control 8, the display 7 or combinations thereof. For example, the direct subsystems, and the management algorithm 6, the control 8, the display 7 or combinations thereof can be in a unitary form factor, such as in a single case or container.

Figure 1B:
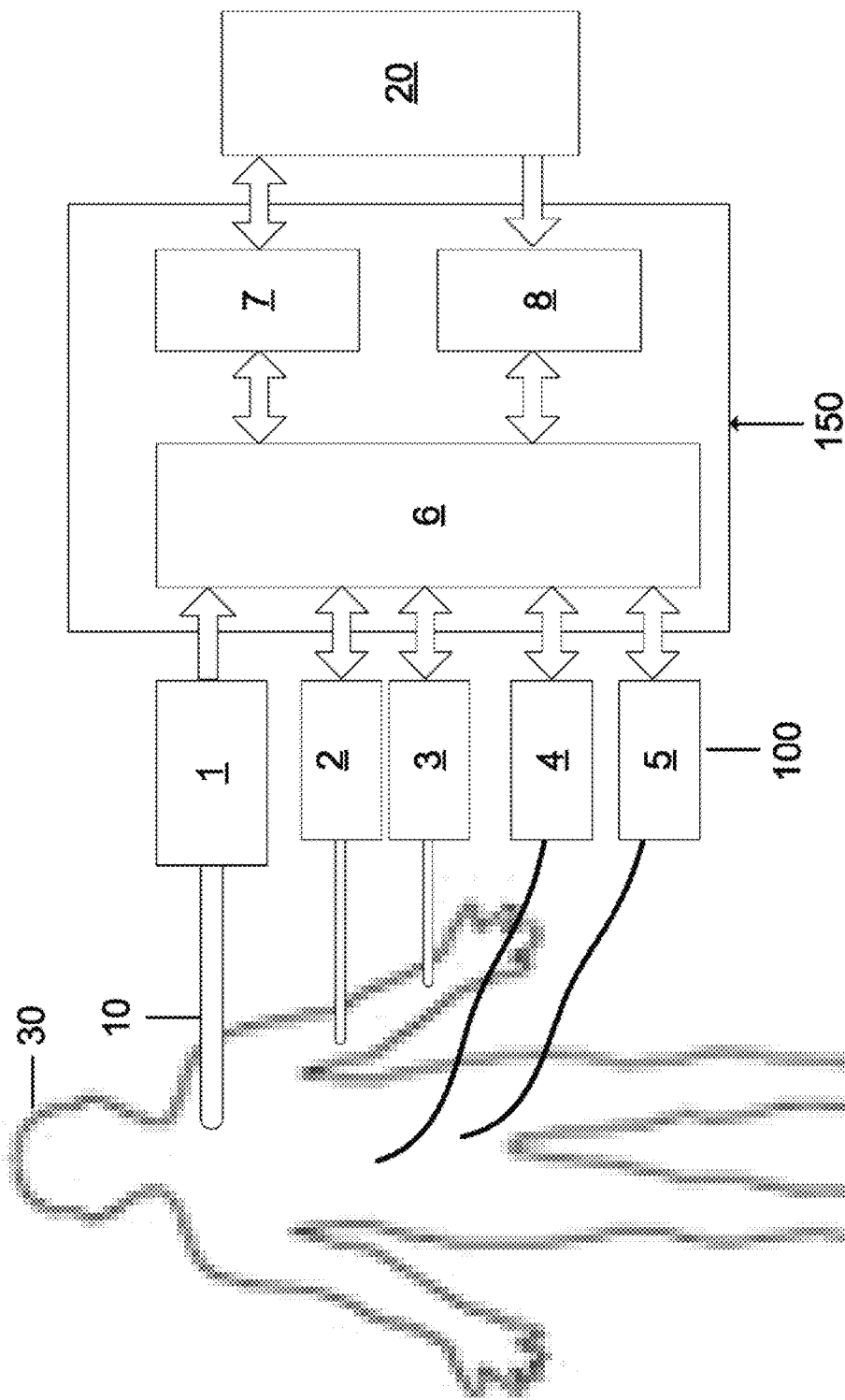

FIG. 1b illustrates that the management system 150 can be physically distinct and separate from the direct subsystems 100. The management system 150 can be in data communication with the direct subsystems 100 through local (e.g., wired) or remote (e.g., wireless) communication. The direct subsystems 100 can be separate physical components that can be releasably connectable to the management system 150 through wired or wireless communication. The direct subsystems 100 can provide data to and/or receive data from the management algorithm 6.

Figure 2A:
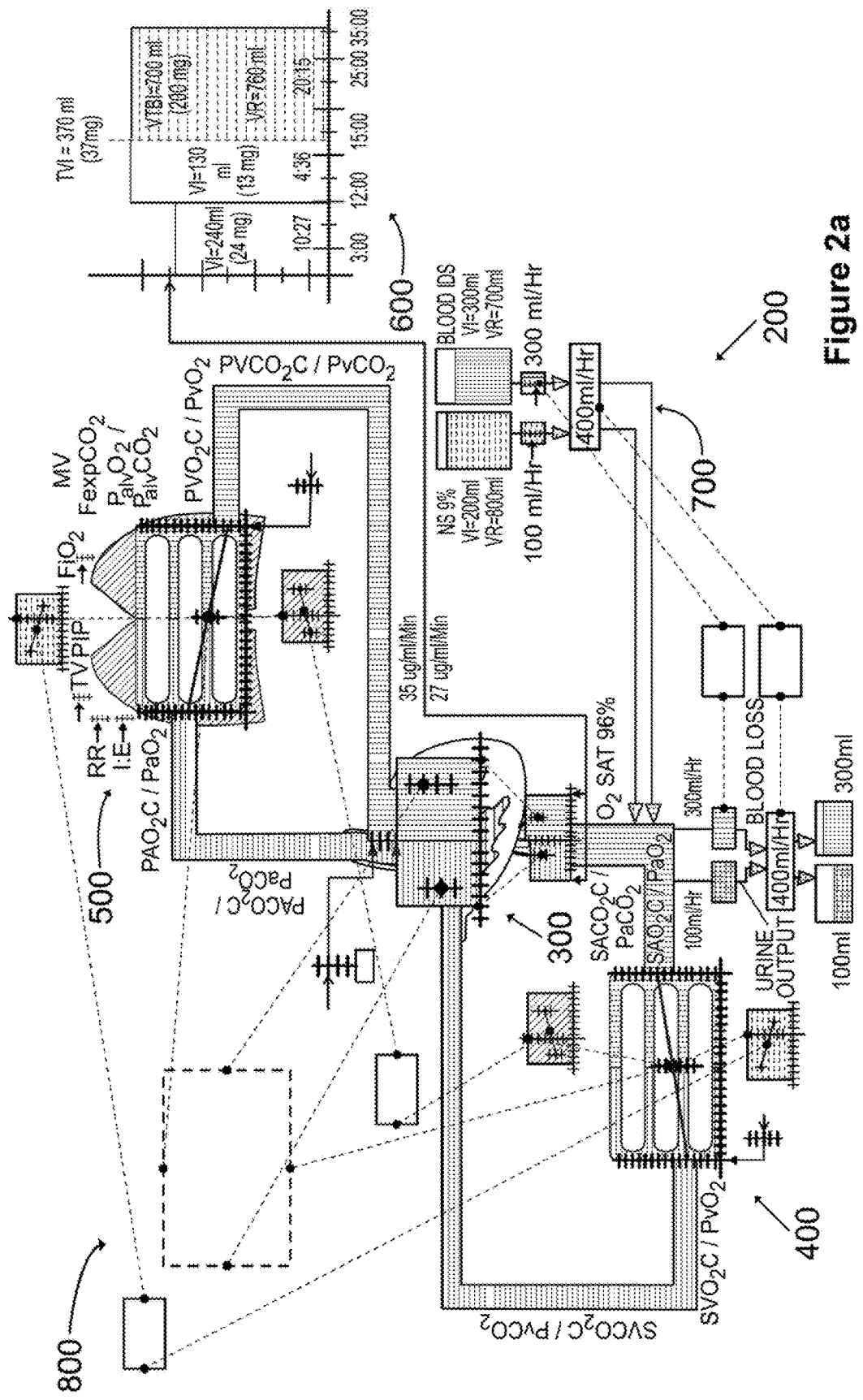
FIG. 2a illustrates a variation of the displays and controls of the patient management system during physiological inspiration.

Display:

FIG. 2a illustrates that the management system 150 can display a management display 200 on the visual display monitor 7. The management display 200 can have a cardiac display 300 that can include a left heart display and a right heart display, a systemic vascular display 400, a pulmonary display 500 that can include a pulmonary vascular display and a ventilation display, a medication administration display or medication graphic object 600, a fluid display 700, a blood flow, oxygenation, and carbon dioxide balance object display 800, or combinations and/or pluralities thereof. The management display 200 can have graphical objects representative of the vascular system connecting the cardiac display 300 to the pulmonary display 500 and/or the systemic vascular display 400 to the cardiac display 300.

The management display 200 can have text labels on the display, for example, the type, quantity and timing of the medications can be shown on the medication administration display 600, and the systemic blood gas measurements can be shown in the graphic object representations of the vascular system.

The management display 200 can be animated to show different states in real-time. For example, the animation can include graphic object changes showing increased lung size in the pulmonary display 500 to indicate inspiration, beating of the heart in the cardiac display or cardiac graphic object 300 to indicate cardiac function, expansion and contraction of the capillaries or vessels in the systemic vascular display 400 to represent vascular dilation, or combinations thereof. The graphic objects indicating medication and fluid levels, the vascular system flow and all other data can also animate during use.

Figure 2B:
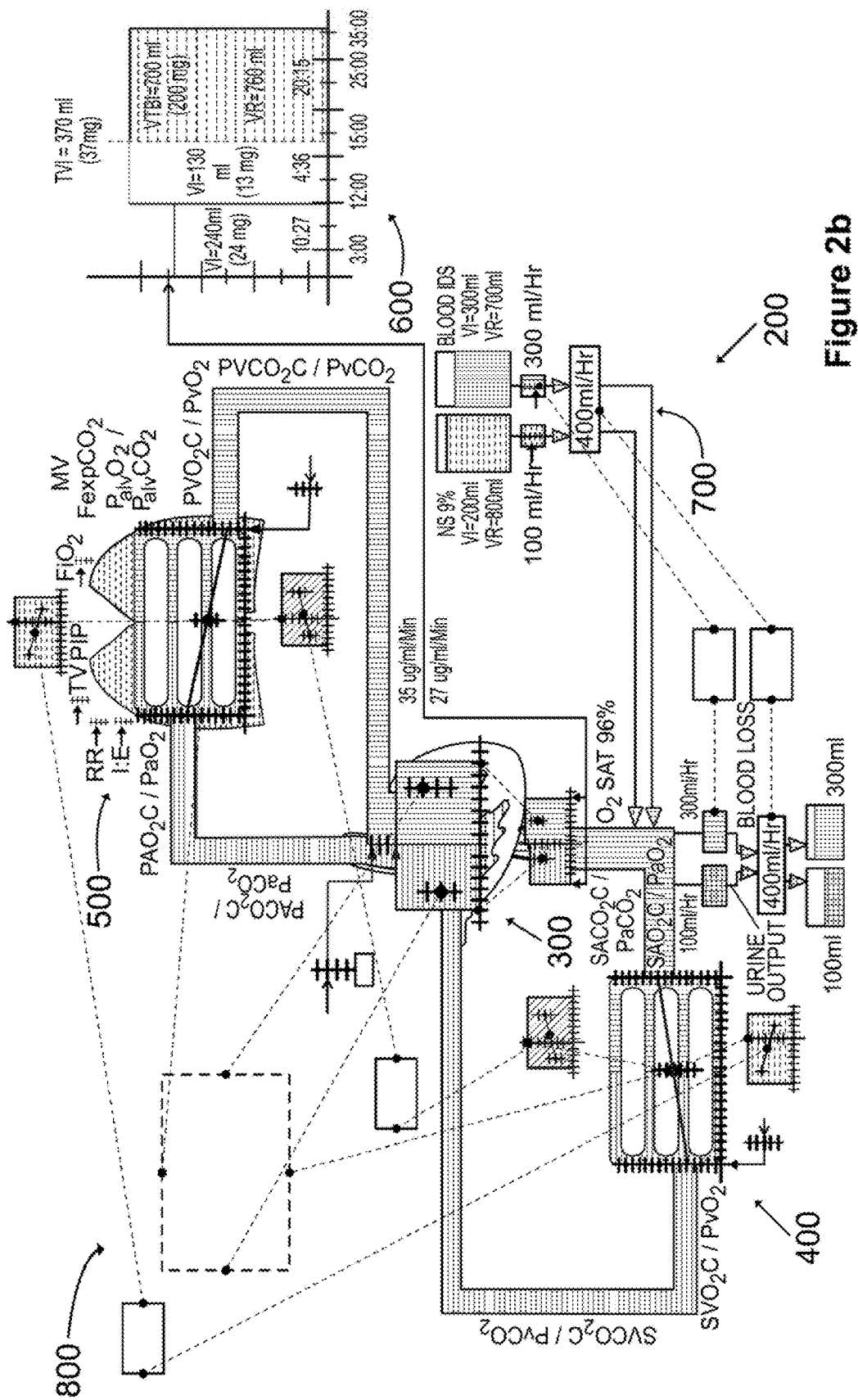
FIG. 2b illustrates the variation of the displays and controls of FIG. 2a during physiological expiration.
Figure 2C:
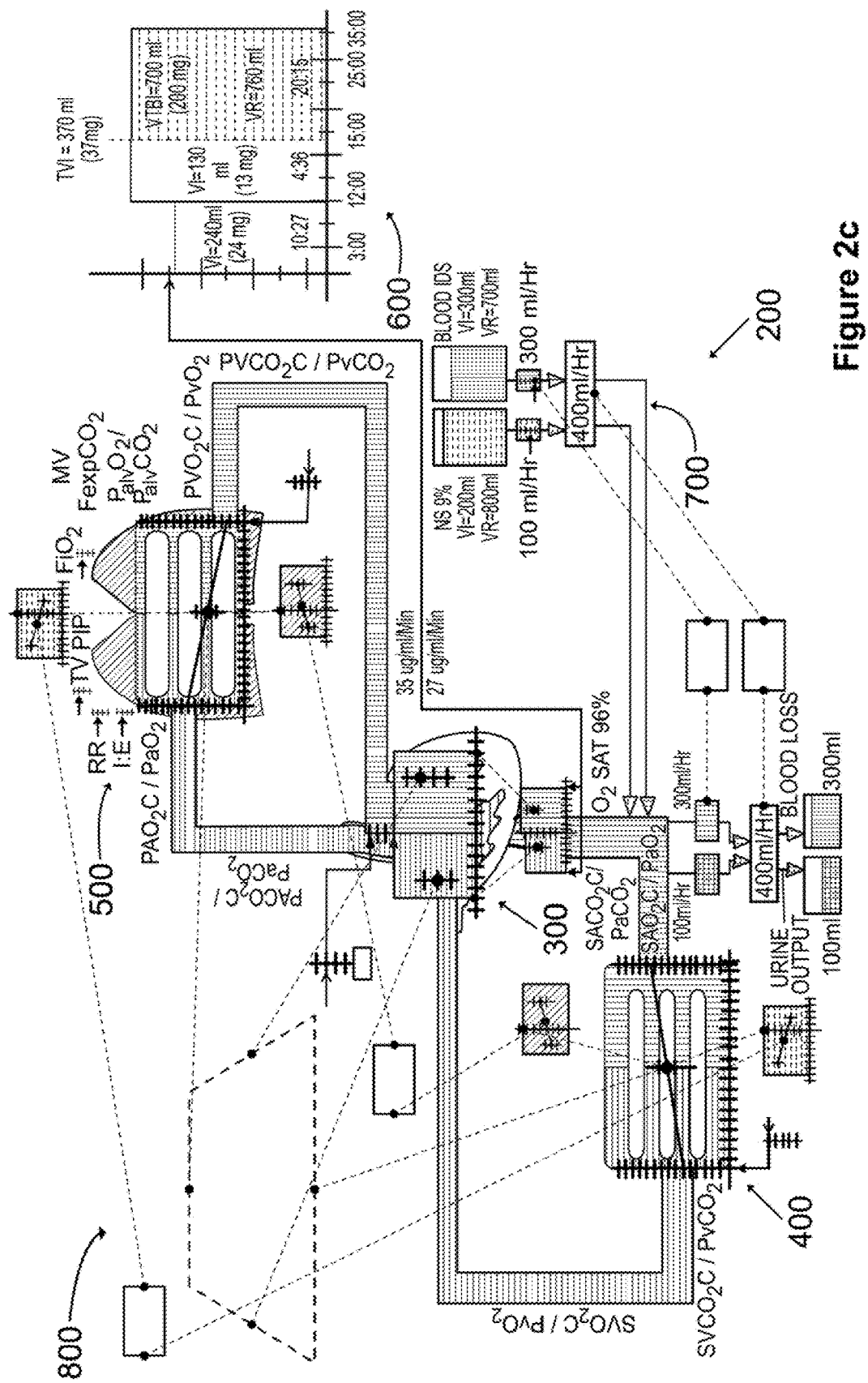
FIG. 2c illustrates the variation of the displays and controls of FIG. 2a during decrease in systemic vascular resistance resulting in increase in systemic vascular blood flow rate.
Figure 2D:
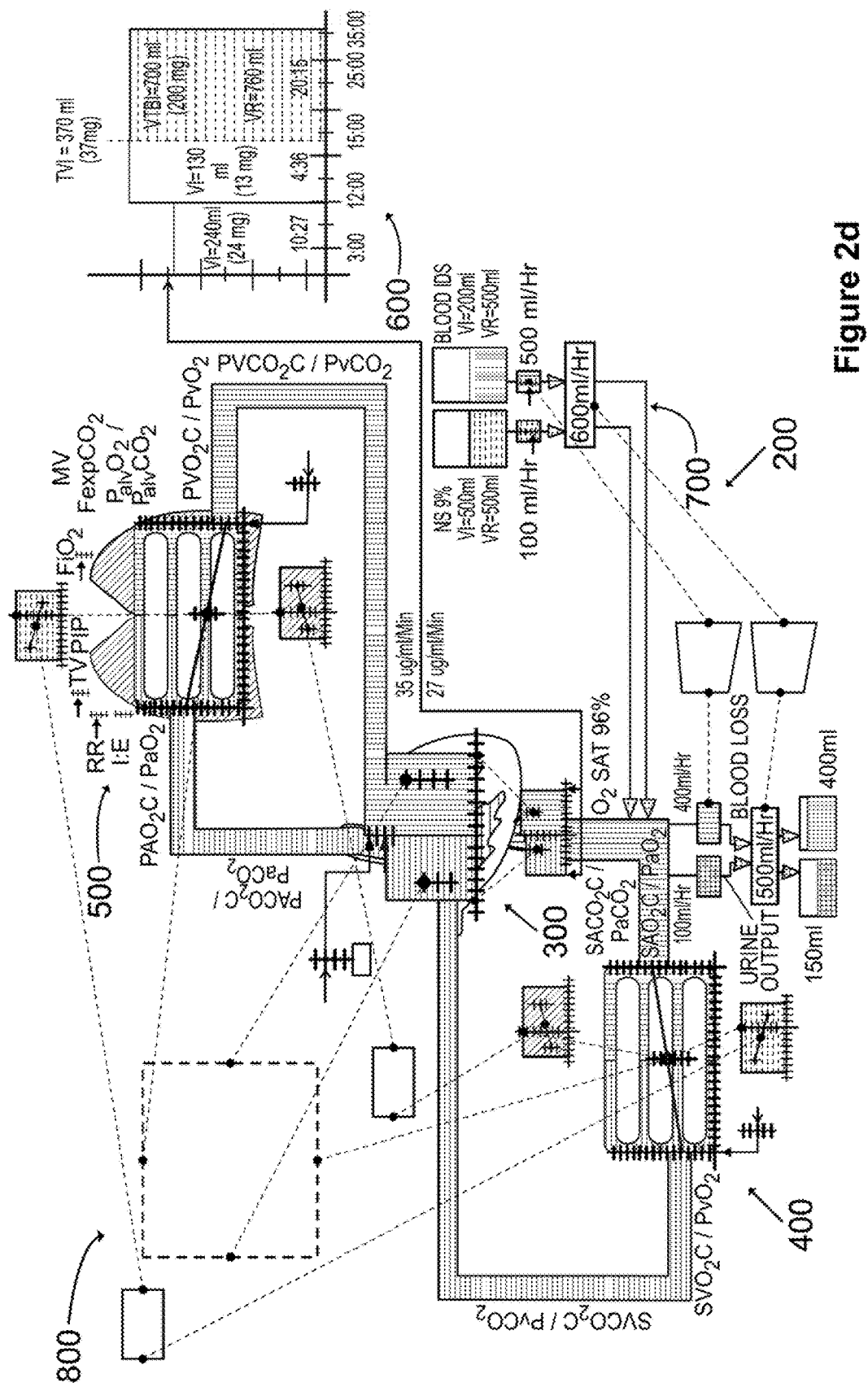
FIG. 2d illustrates the variation of the displays and controls of FIG. 2a during an increase in heart rate resulting in increase in pulmonary and systemic cardiac output.

FIG. 2a illustrates that the management display 200 can be in a first configuration. FIG. 2b illustrates that the management display 200 can be animated to have a second configuration. FIG. 2c illustrates that the management display 200 can be animated to have a third configuration. For example, the systemic vascular display 400 can show increased vascular dilation. The balance control display 800 can alter in shape, reflecting a chance of its components. FIG. 2d illustrates that the fluid delivery settings and levels have changed, the Heart Rate has increased resulting in increased Left Heart and Right Heart cardiac output. The result of increasing Left Heart and Right Heart cardiac output is shown on the cardiac function balance object display 899

Figure 3B:
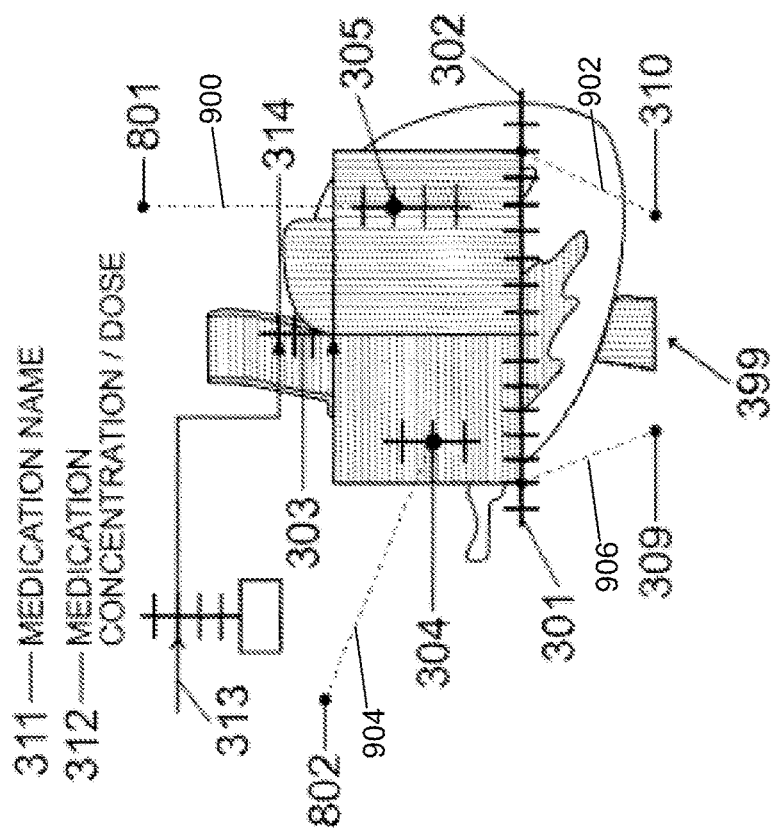
FIG. 3b illustrates a variation of the heart rate and stroke volume displays and controls of the patient management system.
Figure 3A:
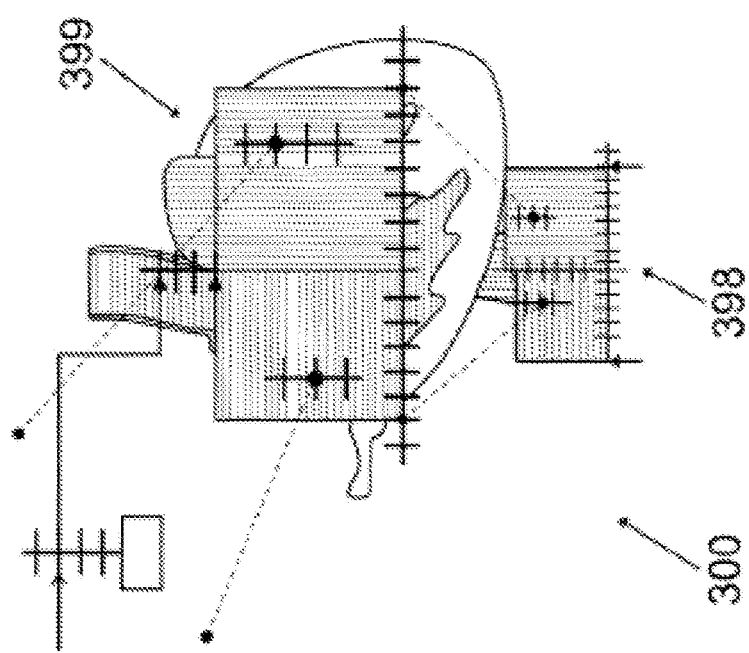
FIG. 3a illustrates a variation of the cardiac displays and controls of the patient management system.

Left Heart Displays:

FIG. 3a illustrates that the cardiac display 300 can have a heart rate and stroke volume display 399 and a contractility and pre-load display 398. The cardiac display 300 shows a graphical representation of the higher-level goals, the middle-level functional parameters, and the lower-level functional parameters and controls used in monitoring and managing the heart including cardiac output, stroke volume, heart rate, contractility, and pre-load. The graphical representation shows interrelationships and interactions between the higher-level goals, the functional parameters, and the lower-level functional parameters and controls used in monitoring and managing the heart including its cardiac output, stroke volume, heart rate, contractility, and pre-load.

The cardiac display 300 can include a left heart display showing a graphical representation of the higher-level goals, the middle-level functional parameters, and the lower-level functional parameters and controls used in monitoring and managing the left heart including its cardiac output, stroke volume, heart rate, contractility, and pre-load. The graphical representation also shows interrelationships and interactions between the higher-level goals, the functional parameters, and the lower-level functional parameters and controls used in monitoring and managing the left heart including its cardiac output, stroke volume, heart rate, contractility, and pre-load.

Left Heart Cardiac Output, Stroke Volume, and Heart Rate Display:

FIG. 3b illustrates that the heart rate and stroke volume display 399 can show a left heart display showing the higher level goal of Left Heart Cardiac Output (LHCO) 305. The LHCO 305 can be projected (i.e., copied) onto the balance display as LHCO 801. The LHCO 305 can be visually linked by line 900 on the display to the LHCO 801 and/or 305.

The functional variables can include Heart Rate (HR), graphed along axis 303, and Left Heart Stroke Volume (LHSV), graphed along axis 302. The variables in the Left Heart Display can be shown and integrated in a graph where the HR value is shown on one axis 303, and the LHSV value is shown on another axis 302 perpendicular to the HR axis. The area of the rectangle along the HR and LHSV values is a measure of the Left Heart Cardiac Output (LHCO) value (HR×LHSV). The LHSV can be projected onto the contractility and pre-load display 398 as LHSV 310. The LHSV represented in the cardiac output display 399 can be visually linked by line 902 on the display to the LHSV 310 on the contractility and pre-load display 398.

An administered medication label 311 and the medication concentration or dose 312 can be shown adjacent to a target or control graph of the medication with a setting level 313. The setting level 313 can be adjusted by the user and/or the management algorithm. Relationships between administered medications and fluids and the functional variables HR and LHSV can be shown by a line 314 connecting between the flow rate or dose of the administered medication or fluid and the HR or LHSV functional parameter or a combination thereof which the medication or fluid has an affect on. The display 399 presents such information onto a graphical representation showing the anatomy of the left heart (e.g., behind the opaque graphs, as shown, or layered with translucent or transparent graphs). The anatomical graphical representation can show the left atrium and ventricle, the aorta, and pulmonary vein.

Right Heart Displays:

The cardiac display 300 can include a right heart display showing a graphical representation of the higher-level goals, the middle-level functional parameters, and the lower-level functional parameters and controls used in monitoring and managing the right heart including its cardiac output, stroke volume, heart rate, contractility, and pre-load. The display also shows interrelationships and interactions between the higher-level goals, the middle-level functional parameters, and the lower-level functional parameters and controls used in monitoring and managing the right heart including its cardiac output, stroke volume, heart rate, contractility, and pre-load.

Right Heart Cardiac Output, Stroke Volume, and Heart Rate Display:

FIG. 3b illustrates that the heart rate and stroke volume display 399 can show the higher level goal represented is Right Heart Cardiac Output (RHCO) 304. The RHCO 304 can be projected onto the balance display as RHCO 802 and/or on the contractility and pre-load display 398 as RHCO 304. The RHCO 304 can be visually linked by line 904 on the display to the RHCO 802.

The functional parameters include Heart Rate (HR), graphed along axis 303, and Right Heart Stroke Volume (RHSV), graphed along axis 301. The higher-level goal and functional parameters in the Right Heart Display are shown and integrated in a graph where the HR value is shown on one axis 303, and the RHSV value is shown on another axis 301 perpendicular to the HR axis. The RHSV can be projected onto the contractility and pre-load display 398 as RHSV 309. The RHSV represented in the cardiac output display 399 can be visually linked by lines 906 on the display to the RHSV 309 on the contractility and pre-load display 398.

The area of the rectangle along the HR and RHSV values is a measure of the Right Heart Cardiac Output value. A measurement of the RHCO 304 is shown on the display. Relationships between administered medications and fluids and the functional parameters HR and RHSV are shown by a line connecting between the flow rate or dose of the administered medication or fluid and the HR or RHSV functional parameter or a combination thereof which the medication or fluid has an affect on. The display presents such information onto a graphical representation of the anatomy of the right heart. The anatomical graphical representation shows the right atrium and ventricle, the pulmonary artery, the superior vena cava, and inferior vena cava.

Figure 3C:
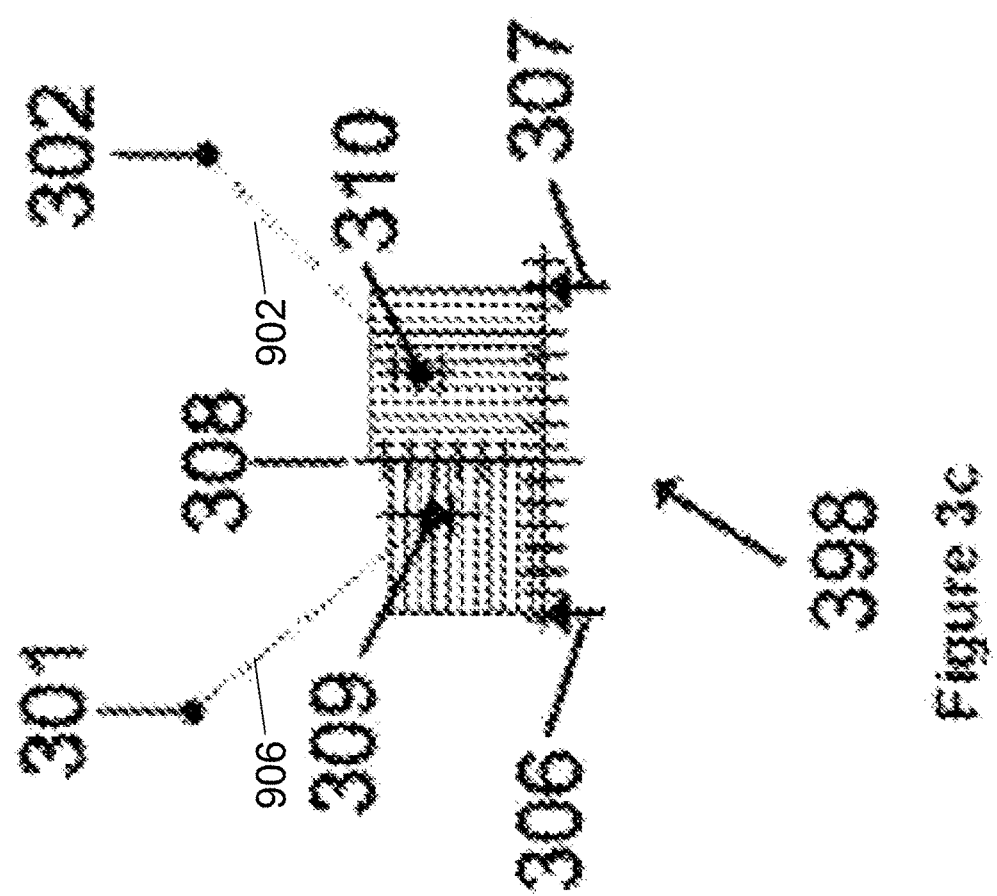
FIG. 3c illustrates a variation the cardiac contractility and pre-load displays and controls of the patient management system.

Left Heart Pre-Load & Contractility Display:

FIG. 3c illustrates that the contractility and pre-load display 398 can have the higher level goal of displaying Left Heart Stroke Volume (LHSV) 310 represented in the cardiac output display 399. The functional variables include pre-load (PL), shown on axis 308, and left heart contractility (CON) 307. The higher-level goal and functional parameters in the display are integrated in a graph where the PL value is shown on one axis 308, and the CON value is shown another axis 307 perpendicular to the PL axis 308. The area of the rectangle along the PL and CON values is a measure of the LHSV 310. A measurement of the LHSV is shown on the Pre-Load and Contractility display 398. The line 902 can connect between the LHSV 310 on the pre-load and contractility display 398 and the LHSV 302 on the cardiac output display 399. Relationships between administered medications and fluids and the functional variables PL and CON are shown by a line connecting between the flow rate or dose of the administered medication or fluid display 700 and the PL or CON functional parameter or a combination thereof which the medication or fluid has an affect on.

Right Heart Pre-Load & Contractility Display:

FIG. 3c illustrates that the contractility and pre-load display 398 can have a higher level goal of displaying right heart stroke volume (RHSV) 309 represented in the cardiac output display 399. The functional parameters include Pre-Load (PL), shown on axis 308 and right heart contractility (CON), shown on axis 306. The higher-level goal and functional parameters in the display are integrated in a graph where the PL value is shown on one axis 308, and the CON value is another axis 306 perpendicular to the PL axis. The area of the rectangle along the PL and CON values is a measure of the RHSV. A measurement of the RHSV is shown on the pre-load and contractility display 398, and the line 906 can connect between the RHSV 309 on the pre-load and contractility display 398 and the RHSV 301 on the cardiac output display 399. Relationships between administered medications and fluids and the functional parameters PL and CON are shown by a line connecting between the flow rate or dose of the administered medication or fluid and the PL or CON functional parameter or a combination thereof which the medication or fluid has an affect on.

Cardiovascular System Displays:

Systemic Vascular Display:

FIG. 4a illustrates that the systemic vascular display 400 can have a systemic vascular blood flow display 498, a systemic oxygenation display 497, a carbon dioxide ($CO_2$) removal display 499, and combinations thereof. The vascular blood flow display 498 can animate to display the increase in diameter of the vessels during decreased vascular resistance.

The systemic vascular display 400 shows a representation of the higher-level goals, the middle-level functional parameters, and the lower-level functional parameters and controls used in monitoring and managing the systemic vascular system including the systemic arterial and venous vascular blood flow, systemic arterial and venous vascular blood pressures, and systemic vascular resistance. The Systemic Vascular Display's graphical representation also shows interactions between the higher-level goals, the middle-level functional parameters, and the lower-level functional parameters and controls used in monitoring and managing the systemic vascular circulatory system including the systemic arterial and venous vascular blood flow, systemic arterial and venous vascular blood pressures, and systemic vascular resistance. The display presents such information onto a graphical representation of the anatomy of the systemic vascular system. The anatomical graphical representation shows the systemic arterial and venous vascular systems.

FIG. 4c illustrates that in the systemic vascular blood flow display 498 the higher level goal represented is systemic blood flow (SBF) 404. The middle-level functional parameters can include Systemic Arterial Pressure (SAP), shown along axis 403, and Systemic Venous Pressure (CVP), shown along axis 402, and the lower-level functional parameters can include the Systemic Vascular Resistance (SVR), shown along axis 419. The higher-level goal and functional parameters in the systemic vascular blood flow display 498 can be shown and integrated in a graph where SAP and CVP values are shown on one axis, and the SVR value is on another axis perpendicular to the SAP and CVP axis. A line connecting between the SAP and CVP values along the SVR axis indicates the systemic blood flow (SBF) 404 value by its slope.

Administered medications can be shown in the systemic vascular blood flow display 498, for example listing the medication name 415 and/or the medication concentration and/or dose 416. Relationships between administered medications and fluids and the functional parameters SAP, CVP, and SVR can be shown by a line 401 connecting between the flow rate or dose of the administered medication or fluid and the functional parameter SAP, CVP, or SVR or a combination thereof which the medication or fluid has an affect on. The graphical object representing the medication can be shown along a dosage axis 418 and can have a target or current dosage rate 417 shown.

The SBF 404 can be projected onto the balance object display 800 as SBF 803. SBF 404 can be linked by a line 912 to SBF 803.

Systemic Oxygen Display:

FIG. 4b illustrates that the systemic vascular display 400 can have a systemic oxygenation display 497. The Systemic Arterial Oxygen Content ($SAO_2C$), shown on axis 406, and the Systemic Blood Flow Rate (SBF) 407 can be used to calculate the Systemic Arterial Oxygen Flow Rate ($SAO_2FR$) 409. The Systemic Venous Oxygen Content ($SVO_2C$), shown on axis 405, and the Systemic Blood Flow Rate (SBF) 407 can be used to calculate the Systemic Venous Oxygen Flow Rate ($SVO_2FR$) 408. An object display is used to show the difference between $SAO_2FR$ 409 and $SVO_2FR$ 407, indicating oxygen Consumption 421.

The oxygen consumption 421 can be projected onto the balance object display 898 as oxygen consumption 805. The oxygen consumption 421 can be linked by a line 914 to the oxygen consumption 805.

Systemic Carbon Dioxide Display:

FIG. 4d illustrates that the systemic vascular display 400 can have a systemic carbon dioxide ($CO_2$) display 499. The systemic $CO_2$ display 499 can show that the Systemic Arterial $CO_2$ Content ($SACO_2C$), shown on axis 411, and the Systemic Blood Flow Rate (SBF) 412 can be used to calculate the Systemic Arterial $CO_2$ Flow Rate ($SACO_2FR$) 414. The Systemic Venous $CO_2$ Content ($SVCO_2C$), shown on axis 410, and the Systemic Blood Flow Rate (SBF) 412 can be used to calculate the Systemic Venous $CO_2$ Flow Rate ($SVCO_2FR$) 413. An object display can be used to show the difference between $SACO_2FR$ 414 and $SVCO_2FR$ 413, indicating $CO_2$ production 420. The $CO_2$ production 420 can be projected onto the balance object display 897 as $CO_2$ production 806. The $CO_2$ production 420 can be linked by a line 916 to $CO_2$ production 806.

Pulmonary Vascular Display:

FIG. 5a illustrates that the pulmonary display 500 can have a pulmonary vascular display 598 and one or more ventilation displays, such as a pulmonary oxygenation display 597 and a pulmonary carbon dioxide display 599.

FIG. 5c illustrates that the pulmonary vascular display 598 shows a representation of the higher-level goals, the middle-level functional parameters, and the lower-level functional parameters and controls used in monitoring and managing the pulmonary vascular system including the pulmonary arterial and venous vascular blood flow, pulmonary arterial and venous vascular blood pressures, and pulmonary vascular resistance. The Pulmonary Vascular Display's graphical representation also shows interactions between the higher-level goals, the middle-level functional parameters, and the lower-level functional parameters and controls used in monitoring and managing the pulmonary vascular system including the pulmonary arterial and venous vascular blood flow, pulmonary arterial and venous vascular blood pressures, and pulmonary vascular resistance. The display presents such information onto a graphical representation of the anatomy of the pulmonary vascular system. The anatomical graphical representation shows representations of the lungs and the pulmonary arterial and venous vascular systems.

The Pulmonary Vascular Display 598 displays the higher level goal of Pulmonary Blood Flow (PBF) 504, the middle-level functional parameters include Pulmonary Arterial Pressure (PAP), shown on axis 502, and Pulmonary Venous Pressure (PcW), shown on axis 503. The lower-level functional parameters include the Pulmonary Vascular Resistance (PVR), shown on axis 532. The higher-level goal and functional parameters in the Pulmonary Vascular Display 598 can be shown and integrated in a graph where PAP and PcW values are shown on one axis, 502 and/or 503, and the PVR value is on another axis 532 perpendicular to the PAP and PcW axis. A line connecting between the PAP and PcW values along the PVR axis 532 indicates the Pulmonary Blood Flow (BPF) 504 by the slope of that line.

The PBF 504 can be projected onto the balance object display 800 as PBF 804. A line 918 can link PBF 504 to PBF 804.

Administered medications can have labels 528 and/or medication concentration and/or dose levels 529 shown. Relationships between administered medications and fluids and the functional parameters PAP, PcW, and PVR are shown by a line 501 connecting between the flow rate or dose of the administered medication or fluid and the functional parameter PAP, PcW, or PVR or a combination thereof which the medication or fluid has an affect on.

The graphical object representing the medication can be shown along a dosage axis 531 and can have a target or current dosage rate 530 shown.

Lungs and Ventilation Display:

The Pulmonary Vascular display 598 can have an anatomical graphical representation of the lungs. The lungs graphical representation can include a Respiratory Rate (RR) 507 on a RR graph 508, Tidal Volume (TV), Alveolar Oxygen Concentration ($F_{alv}O_2$), Inspired Oxygen Concentration ($F_iO_2$), Alveolar $CO_2$ Concentration ($F_{alv}CO_2$), Expired $CO_2$ Concentration ($F_{exp}CO_2$) 516, Minute Ventilation (MV) 515, a ratio of partial pressure of alveolar oxygen to alveolar carbon dioxide ($P_{alv}O_2/P_{alv}CO_2$) 517, or combinations thereof.

Information pertaining to mechanical ventilation can be presented on or around the anatomical lungs graphical representation, for example if the patient is being ventilated mechanically. The display can include ventilation information displays including Respiratory Rate (RR), Tidal Volume (TV), Inspired Oxygen Concentration ($F_iO_2$), Inspiratory Flow Rate, Inspiratory Time, Inspiratory/Expiratory Time Ratio (I:E ratio) 509 on an I:E graph 510, Positive Inspiratory Pressure (PIP) 506 or combinations thereof.

Mapped onto each of the mechanical ventilation variables Respiratory Rate (RR), Tidal Volume (TV) 511 on a TV graph 512, Inspired Oxygen Concentration ($F_iO_2$) 513 on an $F_iO_2$ graph 514, Inspiratory Flow Rate, Inspiratory Time, and Inspiratory/Expiratory Time Ratio (I:E ratio) can be a control for controlling each of the variables. The user can control patient's mechanical ventilation by manipulating controls of the mechanical ventilation variables on the Lungs and Ventilation display including Respiratory Rate (RR), Tidal Volume (TV), Inspired Oxygen Concentration ($F_iO_2$), Inspiratory Flow Rate, Inspiratory Time, Inspiratory/Expiratory Time Ratio (I:E ratio).

Pulmonary Oxygenation Display:

FIG. 5b illustrates that the Pulmonary Oxygenation display 597 can have a Pulmonary Arterial Oxygen Content ($PAO_2C$), shown along the axis 518, and the Pulmonary Blood Flow Rate (PBF) 520 can be used to calculate the Pulmonary Arterial Oxygen Flow Rate ($PAO_2FR$) 521, while the Pulmonary Venous Oxygen Content ($PVO_2C$), shown on the axis 519, and the Pulmonary Blood Flow Rate (PBF) 520 can be used to calculate the Pulmonary Venous Oxygen Flow Rate ($PVO_2FR$) 522. An object display shows the difference between $PAO_2FR$ 521 and $PVO_2FR$ 522, indicating an oxygen transfer rate from the lungs to the blood (Blood Oxygenation 533).

The blood oxygenation 533 can be projected onto the balance object 898. A line 920 can link the blood oxygenation 533 to the blood oxygenation 807.

Ventilation properties can be shown in the graphic objects of the organs themselves, such as on the graphic objects of the vascular system between the organs. On the graphic objects for the vessels within the cardiovascular representation, the systemic arterial oxygen saturation (SaO2SAT), systemic venous oxygen saturation (SvO2SAT), systemic arterial and venous oxygen pressures $PaO_2$, $PvO_2$, pulmonary arterial and venous oxygen pressures $PaO_2$, $PvO_2$, and combinations thereof can be shown.

Pulmonary $CO_2$ Display:

In the Pulmonary $CO_2$ display 599, the Pulmonary Arterial $CO_2$ Content ($PACO_2C$), shown on axis 523, and the Pulmonary Blood Flow Rate (PBF) 525 can be used to calculate the Pulmonary Arterial $CO_2$ Flow Rate ($PACO_2FR$) 526, while the Pulmonary Venous $CO_2$ Content ($PVCO_2C$), shown along axis 524, and the Pulmonary Blood Flow Rate (PBF) 525 can be used to calculate the Pulmonary Venous $CO_2$ Flow Rate ($PVCO_2FR$) 527. An object display shows the difference between $PACO_2FR$ 526 and $PVCO_2FR$ 527, indicating a $CO_2$ mass transfer rate 534 from the blood to the lungs ($CO_2$ Elimination from the blood).

The $CO_2$ mass transfer rate 534 can be projected onto the balance object 897. A line 922 can link the $CO_2$ mass transfer rate 534 to the $CO_2$ mass transfer rate 808.

In the vessels within cardiovascular representation, displayed are the systemic arterial $CO_2$ pressure $PaCO_2$, systemic venous $CO_2$ pressure $PvCO_2$, and pulmonary arterial and venous $CO_2$ pressures $PaCO_2$, $PvCO_2$, respectively.

Ventilation properties can be shown in the graphic objects of the organs themselves, such as on the graphic objects of the vascular system between the organs.

Figure 6:
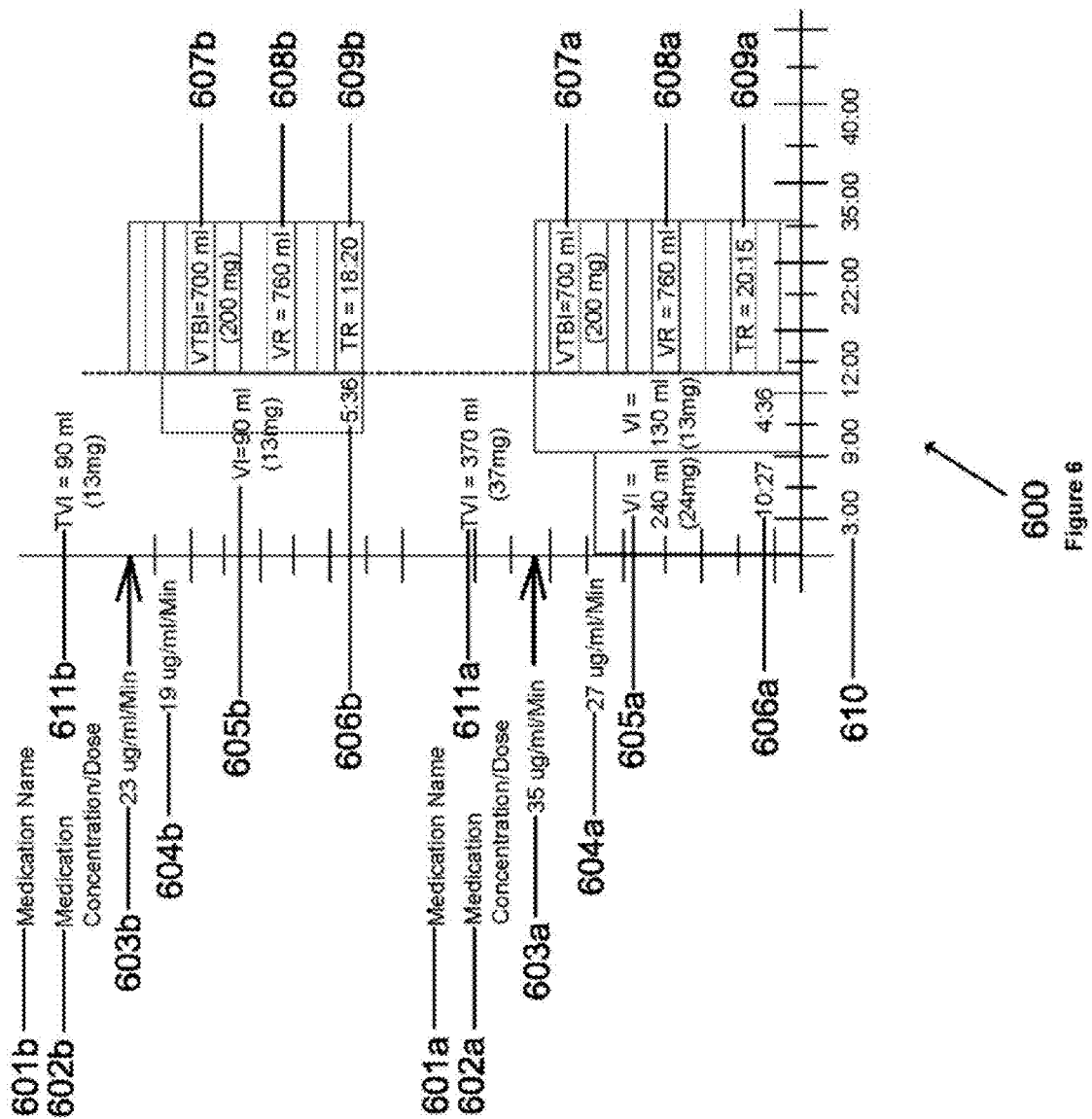
FIG. 6 illustrates a variation of the expanded medications display and controls of the patient management system.

Medication Administration and Management Display:

FIG. 6 illustrates that the Medication Administration and Management Display 600 can display that each medication administered to the patient can be observed, controlled and managed. A display of each administered medication's flow rate and/or dose is shown. The user can select whether to display the medication's flow rate, dose 604 information or a combination thereof. The user can select what time of day to administer the medication, as shown by the horizontal axis 610 labeled with times. Mapped onto the medication flow rate 604 information is the medication's flow rate control or regulator 603 (e.g., can be shown as an arrow on the touch screen display 7). The user can manipulate the medication's flow rate control (regulator) 603 to adjust the medication's flow rate (i.e., increase or decrease the flow rate setting). Mapped onto the medication dose information 604 is the medication's dose control or regulator 603. The user can manipulate the medication's dose control (regulator) 603 to adjust the medication's dose (i.e., increase or decrease the dose setting).

A line can connect between each medication's flow rate or dose control (regulator) 603 and the cardiovascular functional parameter which the medication has an affect on. For example, vasoconstrictive medications can have a line connecting between the medication's flow rate or dose control (regulator) 603 and the systemic vascular resistance (SVR) 401 or pulmonary vascular resistance (PVR) 501 on the cardiovascular display or a combination thereof. Medications which affect the heart rate 303 can have a line connecting between the medication's flow rate or dose control (regulator) 603 and the heart rate 303 value on the cardiovascular display.

Expanded Medication Administration and Management Display:

For each administered Medication, the user can select to expand or collapse the medication's administration and management display 600. In the expanded Medication Administration and Management Display 600, the medication's flow rate and/or dose values 604a,b can be displayed on one axis, while time 610 is shown on another perpendicular axis. The user can choose to display the medication's flow rate or dose or both. The area under the flow rate or dose 604a,b vs. time 610 graph represents the medication's volume or amount (mass) 605a,b, respectively. Mapped onto the medication flow rate or dose information 604a,b is the medication's flow rate or dose control or regulator 603a,b, respectively. The user can manipulate the medication's flow rate or dose control (regulator) to adjust the medication's flow rate or dose, respectively (i.e., increase or decrease the flow rate or dose setting, respectively). A line connects between each medication's flow rate or dose control (regulator) 603a,b and the cardiovascular functional parameter which the medication has an affect on.

In combination with the medication flow rate and/or dose and time information, the flow rate/dose vs time display shows the medication's name 601a,b, concentration 602a,b, volume and/or amount to be infused to the patient 607a,b, volume and/or amount administered to the patient 611a,b, period of medication administration 606a,b, remaining volume and/or amount to be infused or administered to the patient 608a,b, remaining time to complete medication administration at the currently set flow rate or dose 609a,b, and the total volume and/or amount of medication remaining in the reservoir 608a,b.

Target-Controlled (Model-Driven) Infusion Pump Display:

A medication management display 600 can be used for medications infused by target-controlled or model-driven "smart" infusion pumps. The medication management display 600 can have a display showing the medication's flow rate or dose information 604a,b, as well as the medication's name 601a,b, concentration 602a,b, total volume and/or amount, volume and/or amount administered to the patient

611*a,b*, period of medication administration, remaining volume (i.e., volume to be infused "VTBI") 607*a,b*, (volume infused "VI") 605*a,b*, (total volume infused) TVI 611*a,b*. and/or amount to be infused or administered to the patient, remaining time to complete medication administration at the currently set flow rate or dose ("TR") 609*a,b*, and the total volume and/or amount of medication remaining in the reservoir ("VR") 608*a, b*. Mapped onto the medication flow rate or dose information is the medication's flow rate or dose control or regulator 603, respectively. The user can manipulate the medication's flow rate or dose control (regulator) to adjust the medication's flow rate or dose (as shown by target dose controls 604*b*, 604*a*), respectively (i.e., increase or decrease the flow rate or dose setting, respectively).

For each cardiovascular functional parameter 303 which is affected and controlled by a medication being administered using a target-controlled or model-driven infusion pump, a control or regulator 314 of the cardiovascular functional parameter is mapped onto its measurement value on the cardiovascular display. The cardiovascular display then shows both the measured 303 and target (set/desired) 314 values of the cardiovascular functional parameter.

The user can adjust the cardiovascular functional parameter's target, set or desired value 314 by manipulating the medication delivery control 313 on the target control pump anywhere in the management display (e.g., within the cardiovascular display, pulmonary display, systemic vascular display) which in turn will automatically control and adjust the flow rate or dose of the medication or medications which affect this (e.g., cardiovascular, pulmonary, systemic vascular) functional parameter.

The functional parameter can be adjusted to control the infusion pump. For example, a target functional parameter can be entered through the control 8. The target functional parameter can be processed by the management algorithm 6, which in turn can automatically control and adjust the flow rate or dose of the medication or medications which affect this (e.g., cardiovascular, pulmonary, systemic vascular) functional parameter. For example, a smart infusion pump can be used to control delivery of the medication to the patient.

As an example, a line connects between the cardiovascular functional parameter's control or regulator on the cardiovascular display and the flow rate or dose information on the medication display of the medication or medications which affect the cardiovascular functional parameter. The target-controlled or model-driven infusion pump system monitors the cardiovascular functional parameter's measured value and adjusts the medication's flow rate or dose automatically to achieve the set or desired cardiovascular functional parameter value. For example, when the user adjusts the target or desired heart rate value 314 on the cardiovascular display, the pump adjusts the flow rate or dose of the medication or medications which control the heart rate accordingly to achieve the desired heart rate value. The pump system monitors the heart rate value and adjusts the medication's flow rate automatically to achieve the desired heart rate value. Similarly, when the user adjusts the left heart stroke volume (LHSV) or contractility values on the cardiovascular display, the pump adjusts the flow rate or dose of the medication or medications which affect LHSV or contractility, respectively.

Medication Administration and Management Graphical Display & Animation:

Each medication being administered to the patient is represented graphically by displaying an image of the medication's reservoir such as an image of a medication bag, bottle, or syringe. On the image representing the medication displayed is the medication's name, concentration, total volume and/or amount, administration flow rate and/or dose, period of medication administration, remaining volume and/ or amount to be infused or administered to the patient, remaining time to complete medication administration at the currently set flow rate or dose, and the total volume and/or amount remaining in the reservoir.

A line representing the administered medication's flow in a clear plastic tubing routes from the medication's reservoir to its administered location on the patient's vascular system's anatomical graphical representation within the cardiovascular display. This line has a similar color to the medication's color (e.g., gray for a clear color medication) and connects between each administered medication reservoir and its administration location on the patient's vascular system's anatomical graphical representation within the cardiovascular display. The medication line can be animated to show the medication flowing in a plastic tubing from its reservoir bag to its administered location on the patient's vascular system's anatomical graphical representation within the cardiovascular display. Higher medication flow rate is represented by a medication line moving at a faster rate.

A display of the medication's flow rate and/or dose is shown on the medication's reservoir and/or anywhere on the medication line connecting between the medication's reservoir and its administration location on the patient's vascular system's anatomical graphical representation within the cardiovascular display.

Patient's Fluids Administration and Management Display:

FIG. 7 illustrates that the fluid management display 700 can display, control, and manage any or all fluids administered to the patient including IV solutions, blood, etc. Also, all fluids collected from the patient such as urine and blood loss are all displayed and managed in this display. For each administered fluid, displayed are the fluid's name 701*a,b*, administration flow rate 704*a,b*, volume infused 702*a,b*, volume to be infused 703*a,b*, time remaining to complete fluid administration at the currently set rate, and volume remaining in the fluid reservoir (bag, syringe, bottle, etc.). Mapped onto the fluid administration flow rate 704*a,b* is the fluid's flow rate control or regulator 713*a,b*. The user can control and adjust the fluid's flow rate by manipulating its flow control or regulator to increase or decrease the fluid flow rate value. In this flow rate control, the user can move the flow rate value indicator from the current flow rate value to the desired flow rate value. When several fluids are being administered to the patient, a Total Inflow Rate (TIFR) 705 is calculated and displayed by the system.

In the Fluids Administration and Management Display 700 all fluids collected from the patient are displayed and managed such as urine collected from the patient and blood loss, etc. For each fluid being collected from the patient, displayed are the fluid's name, collection flow rate 706, 707, and volume collected 709, 710. When several fluids are being collected from the patient, a Total Outflow Rate (TOFR) 708 can be calculated and displayed by the system.

Inflow and Outflow Fluids Balance Display:

The Inflow and Outflow Fluids Balance display 712 shows balance information between fluids being administered to the patient (inflow fluids) and fluids being collected from the patient (outflow fluids) using one or multiple object displays. Each fluid balance object display shows balance information both graphically and numerically by displaying information such as difference or % difference between inflow and outflow rate values for inflow and outflow fluids, and difference or % difference between inflow and outflow volumes (e.g., volume administered to patient and volume collected from patient) for inflow and outflow fluids.

The user can select which inflow and outflow fluids to be incorporated in any fluids balance object display 700. For example, the user could select blood collected from the patient (i.e., blood loss) and blood and IV solutions administered to the patient to be incorporated in a blood fluid balance object display 711. If multiple inflow and/or outflow fluids are incorporated in one fluids balance object display, a second balance object display is displayed showing balance information between TIFR and TOFR values and/or between total administered volume and total collected volume for the inflow and outflow fluids.

Balance Object Display:

FIG. 8a illustrates that the balance object display 800 can have a blood flow balance object display 899, an oxygenation balance object display 898 and a carbon dioxide balance object display 897.

The balance object display 800 can have integral or configurate displays. For example, the balance object display can show interactions and balance information among the higher-level goals of managing the cardiovascular, pulmonary and fluid systems.

FIG. 8b illustrates that the blood flow balance object display can display SBF 803, PBF 804, LHCO 801, and RHCO 802 as an object or integral display. The blood flow balance object display can integrate the SBF 803, PBF 804, LHCO 801, and RHCO 802 into one object. In the blood flow balance object display 899, each of the SBF 803, PBF 804, LHCO 801, and RHCO 802 or a function thereof is represented as a part of an object (e.g., a side of a rectangle or triangle). When the different parts are combined together they form a certain shape of a certain object which can be used by the user to quickly deduct the relationships between SBF 803, PBF 804, LHCO 801, and RHCO 802. For example, if each of the SBF 803, PBF 804, LHCO 801, and RHCO 802 is represented as a side of a rectangle object, then the object display formed by the combination of the different parts will be a rectangle. The shape of the rectangle is a graphical representation of the balance between SBF 803, PBF 804, LHCO 801, and RHCO 802. For example, if SBF 803, PBF 804, LHCO 801, and RHCO 802 are all equal, then the object display 899 formed will be a square which can be used by the user to quickly deduct the relationships between SBF 803, PBF 804, LHCO 801, and RHCO 802.

FIG. 8c illustrates that the oxygenation balance object display 898 can have oxygen consumption 805 and blood oxygenation 807. As long as the oxygen consumption 805 and the blood oxygenation 807 remain substantially in balance, the oxygenation balance object display 898 can maintain an expected (e.g., rectangular) configuration. If the oxygen consumption 805 or the blood oxygenation 807 become out of balance, then the configuration of the oxygenation balance object display 898 can alter to become a configuration to denote irregularities (e.g., circular, overly elongated, etc.) to the user.

FIG. 8d illustrates that the carbon dioxide balance object display 897 can have $CO_2$ production 806 and $CO_2$ removal 808. As long as the $CO_2$ production 806 or $CO_2$ removal 808 remain substantially in balance, the carbon dioxide balance object display 897 can maintain an expected (e.g., rectangular) configuration. If the $CO_2$ production 806 or $CO_2$ removal 808 become out of balance, then the configuration of the carbon dioxide balance object display 897 can alter to become a configuration to denote irregularities (e.g., circular, overly elongated, etc.) to the user.

Animation

Cardiovascular Display Animation:

The cardiovascular graphical representation is also animated showing the heart beating (contracting) at the measured HR value. The LHSV and RHSV measurements can be shown in the animation by the size of expansion of the left and right ventricles, respectively. The blood can also be shown circulating through out the cardiovascular system including the left and right hearts and systemic and pulmonary vascular systems. The blood in the left heart, the systemic arterial vascular system, and the pulmonary venous vascular system is shown in red color to indicate blood oxygenation. The blood flowing in the right heart, the pulmonary arterial vascular system, and the systemic venous vascular system is shown in blue color to indicate blood de-oxygenation. The intensity of the blood's red and blue colors can indicate the systemic and pulmonary arterial and venous $O_2$ and $CO_2$ contents, systemic $P_aO_2$, $P_vO_2$, $P_aCO_2$, and $P_vCO_7$ and pulmonary $P_aO_2$, $P_vO_2$, $P_aCO_2$, and $P_vCO_2$.

Lungs Display Animation:

The lungs graphical representation can be animated to show the lungs expand or inflate to mimic inspiration and deflate to mimic expiration. The patient's RR is animated by the rate at which the lungs expand and deflate, while the TV measurement is animated by the size of lungs' expansion. The lungs' color during inspiration (i.e., lungs' expansion) can turn to green to indicate alveolar oxygenation, while lungs' color during expiration (lungs' deflation) can turn to gray to indicate $CO_2$ transfer to the lungs. The intensity or saturation of the lungs' green color can graphically represent the $F_{alv}O_2$ or $F_iO_2$ values. The intensity or saturation of the lungs' gray color can graphically represent the $F_{alv}CO_2$ or $F_{exp}CO_2$ values. Higher $F_{alv}O_2$ or $F_iO_2$ values are represented by a more intense or saturated green color, and lower $F_{alv}O_2$ or $F_iO_2$ values are represented by a less intense or saturated green color. Similarly, higher $F_{alv}CO_2$ or $F_{exp}CO_2$ values are represented by a more intense or saturated gray color, and lower $F_{alv}CO_2$ or $F_{exp}CO_2$ values are represented by a less intense or saturated gray color.

Fluids Administration and Management Graphical Display and Animation:

Each fluid being administered to the patient is represented graphically by displaying an image of the fluid's reservoir such as an image of a blood or IV solution bag. On the image representing the fluid being administered, displayed is the fluid's name, concentration or dose information, total volume, administration flow rate, time remaining to complete fluid administration at the set flow rate, remaining volume to be infused or administered to the patient, and the total volume remaining in the reservoir. Displayed also is a line representing the administered fluid's flow in a clear plastic tubing from the fluid's reservoir to its administered location on the patient's vascular system within the cardiovascular display. This line has a similar color to the fluid's color (e.g., gray for IV saline solution, red for blood) and connects between each administered fluid reservoir and its administered location on the patient's vascular system within the cardiovascular display. The fluid line can be animated to show the fluid flowing in the plastic tubing from its reservoir bag to its administered location on the patient's vascular system within the cardiovascular display. Higher fluid flow rate is represented by a fluid line moving at a faster rate. A measurement of the fluid's administration flow rate is displayed on the fluid's reservoir and/or anywhere on the fluid line connecting between the fluid's reservoir and its administered location on the patient's vascular system within the cardiovascular display. Mapped onto the fluid administration flow rate value is the fluid's flow rate control or regulator. The user can control and adjust the fluid's flow rate by manipulating its flow control or regulator to increase or decrease the fluid flow rate value. In this flow rate control, the user can move the flow rate value indicator from the current flow rate value to the desired flow rate value.

When several fluids are being administered to the patient, a Total Inflow Rate (TIFR) value is calculated and displayed by the system. For each of the administered fluids, a first fluid line connects between the fluid's reservoir and the TIFR value, while a second fluid line connects between the TIFR value and the fluids' administered location on the patient's vascular system within the cardiovascular display. The first and second fluids lines for each of the administered fluids can be animated as described above to graphically show the fluid's flow rate. For each of the administered fluids, a measurement of the fluid's flow rate value is displayed on the fluid's reservoir and/or anywhere on the first fluid line connecting between its reservoir and the TIFR value. Mapped onto each of the fluid's flow rate value is the fluid's flow rate control or regulator. The user can control and adjust the fluid's flow rate by manipulating its flow control or regulator to increase or decrease the flow rate value. In this flow rate control, the user can move the flow rate value indicator from the current flow rate value to the desired flow rate value.

Each fluid being collected from the patient is represented graphically by displaying an image of the fluid's collection reservoir such as an image of a blood collection canister or a urine collection bag. On or adjacent to the image representing the fluid displayed is the fluid's name, collected volume, and collection flow rate. Displayed also is a line representing the collected fluid flowing in a plastic tubing from the fluid's source on the patient's vascular system within the cardiovascular display to its collection reservoir. This line has a similar color to the fluid's color (e.g., yellow for urine, red for blood) and connects between each collected fluid's source location on the patient's vascular system within the cardiovascular display and its collection reservoir. The fluid line can also be animated as described above to show the fluid flowing from its source location on the patient's vascular system within the cardiovascular display to its collection reservoir. Higher fluid flow rate is represented by a fluid line moving at a faster rate. For each of the fluids being collected from the patient, a measurement of the fluid's collection flow rate is displayed on the fluid's collection container and/or anywhere on the fluid line connecting between its source location on the vascular system within the cardiovascular display and its collection reservoir.

When several fluids are being collected from the patient, a Total Outflow Rate (TOFR) value is calculated and displayed by the system. For each of the collected fluids, a first fluid line connects between the fluids' collection source on the patient's vascular system within the cardiovascular display and the TOFR value, while a second fluid line connects between the TOFR value and the fluid's collection reservoir. The first and second fluid lines for collected fluids can be animated as described above to mimic and graphically represent the flow rate value for each of the collected fluids. For each of the collected fluids, a measurement of the fluid's collection flow rate value is displayed on the fluid's collection reservoir and/or anywhere on the first fluid line connecting between its collection source location on the patient's vascular system within the cardiovascular display and the TOFR value.

Any labels shown or other text data shown on the display can be shown on, in, or adjacent to the representative graphic to which that label or text data is associated. Exemplary labels and text data are shown throughout the figures for illustrative purposes.

Any combinations or pluralities of elements herein are disclosed. The descriptions herein are exemplary and not intended to be limiting in any way.

I claim:

1. A method for displaying integrated graphics for diagnostics for a patient's physiology, the method comprising:
    displaying a cardiac graphic object representing cardiac performance based on at least one measurement from the patient's left ventricle performance, said cardiac graphic object including at least a first, second, and third physiological parameter;
    displaying at least one dynamic graphical line from the first physiological parameter being displayed to the second physiological parameter being displayed, and wherein the displaying of the dynamic graphical line comprises illustrating at least one functional relationship between the first and second physiological parameters;
    displaying a pulmonary graphic object representing pulmonary performance, wherein displaying the pulmonary graphic object comprises displaying pulmonary vascular blood flow, and wherein the displaying the pulmonary vascular blood flow comprises displaying at least one measurement based on the patient's pulmonary arterial blood pressure and at least one measurement based on the patient's pulmonary venous blood pressure, and at least one measurement based on the patient's pulmonary vascular resistance; and
    displaying a systemic vascular graphic object representing systemic cardiovascular performance, wherein displaying the systemic vascular graphic object comprises displaying systemic vascular blood flow, wherein the displaying the systemic vascular blood flow comprises displaying at least one measurement based on the patient's systemic arterial blood pressure and at least one measurement based on the patient's systemic venous blood pressure, and at least one measurement based on the patient's systemic vascular resistance.

2. The method of claim 1, wherein the cardiac graphic object is also based on at least one measurement from the patient's right ventricle performance.

3. The method of claim 1, wherein displaying the cardiac graphic object comprises displaying cardiac output, and wherein the displaying the cardiac graphic output comprises displaying a graph displaying stroke volume and heart rate.

4. The method of claim 3, wherein the graph displaying stroke volume comprises displaying a left ventricle stroke volume and a right ventricle stroke volume.

5. The method of claim 3, further comprising displaying a physiologic performance target.

6. The method of claim 5, further comprising displaying a physiologic performance target-controlled medication delivery correlated with the physiologic performance target.

7. The method of claim 3, further comprising displaying a contractility graphic object representing a contractility quotient based on a pre-load and/or contractility of the patient's heart.

8. The method of claim 7, wherein the contractility graphic object represents the pre-load and/or contractility of the patient's heart correlated with a medication delivery.

9. The method of claim 1, wherein displaying the pulmonary graphic object comprises displaying a oxygenation and $CO_2$ removal performance.

10. The method of claim 1, wherein displaying the systemic vascular graphic object comprises displaying a systemic oxygen consumption and CO2 production performance.

11. The method of claim 1, further comprising displaying a medication delivery and controlling a delivery of at least one medication to the patient through the display, wherein the controlling of the delivery of the at least one medication comprises automatically controlling the medication delivery by a processor.

12. The method of claim 11, wherein the controlling of the delivery of the at least one medication comprises setting a physiological performance target.

13. The method of claim 1, displaying a net fluid flow graphic representing a fluid inflow to the patient and an outflow from the patient, wherein displaying a net fluid flow graphic comprises displaying urine output and blood loss, and/or displaying blood flow input and intravenous fluid administration, and/or displaying a net fluid flow balance object display.

14. The method of claim 1, wherein any one of the cardiac graphic object, the pulmonary graphic object, or the systemic vascular graphic object comprises an animated graphic.

15. The method of claim 1, wherein displaying the pulmonary graphic object comprises displaying a ventilation performance.

16. The method of claim 15, wherein displaying a ventilation performance comprises displaying a measurement of tidal volume, and/or alveolar oxygen concentration, and/or inspired oxygen concentration, alveolar CO2 concentration, and/or expired CO2 concentration, and/or minute ventilation, and/or a ratio of partial pressure of alveolar oxygen to alveolar carbon dioxide, and/or respiratory rate, and/or inspiratory flow rate, and/or inspiratory time, and/or inspiratory-to-expiratory time ratio, and/or positive inspiratory pressure.

17. The method of claim 1, wherein displaying the cardiac graphic object further comprises displaying at least one measurement based on a left heart cardiac output, displaying at least one measurement based on a right heart cardiac output, displaying at least one measurement based on a heart rate, displaying at least one measurement based on a contractility, and displaying at least one measurement based on a pre-load.

18. The method of claim 1, wherein displaying the pulmonary graphic object comprises displaying at least one measurement based on a pulmonary blood flow rate, and wherein displaying the systemic vascular graphic object comprises displaying at least one measurement based on a vascular blood flow rate.

19. A method for displaying integrated graphics for diagnostics for a patient's physiology, the method comprising:
displaying a cardiac graphic object representing cardiac performance based on at least one measurement from the patient's left ventricle performance, wherein the displaying of the cardiac object comprises displaying an anatomical graphical representation of the cardiovascular system, and wherein the anatomical graphical representation of the cardiovascular system is animated and beats at a measured heart rate value;
displaying a medication graphic object representing delivery of at least one medication to the patient; and
displaying a physiological parameter in the cardiac graphic object.

20. A method for displaying integrated graphics for diagnostics for a patient's physiology, the method comprising:
displaying a cardiac graphic object representing cardiac performance based on at least one measurement from the patient's left ventricle performance, wherein the cardiac performance comprises the systemic arterial pressure, the systemic venous pressure, and the cardiovascular resistance, and wherein the displaying of the cardiac graphic object comprises displaying an anatomical graphical representation of the cardiovascular system;
displaying a medication graphic object representing delivery of at least one medication to the patient;
displaying at least one dynamic graphical line from a first physiological parameter being displayed to a second physiological parameter being displayed, at least one dynamic graphical line illustrates at least one functional relationship between the first and second physiological parameters; and
displaying a secondary graphic object, wherein the secondary graphic object comprises at least one of a pulmonary graphic object representing pulmonary performance and a systemic vascular graphic object representing systemic vascular performance, wherein the secondary graphic object comprises an anatomical representation of the respective anatomical system;
wherein the cardiac graphic object and the secondary graphic object are displayed simultaneously.

* * * * *